US011478266B2

(12) United States Patent
Bjursten

(10) Patent No.: US 11,478,266 B2
(45) Date of Patent: *Oct. 25, 2022

(54) TISSUE CUTTING DEVICE AND SYSTEM

(71) Applicant: Septulus AB, Lund (SE)

(72) Inventor: Henrik Bjursten, Lund (SE)

(73) Assignee: Septulus AB, Lund (SE)

( * ) Notice: Subject to any disclaimer, the term of this patent is extended or adjusted under 35 U.S.C. 154(b) by 256 days.

This patent is subject to a terminal disclaimer.

(21) Appl. No.: 16/810,433

(22) Filed: Mar. 5, 2020

(65) Prior Publication Data

US 2020/0281620 A1 Sep. 10, 2020

Related U.S. Application Data

(63) Continuation of application No. 15/570,451, filed as application No. PCT/EP2016/059590 on Apr. 29, 2016, now Pat. No. 10,610,249.

(30) Foreign Application Priority Data

Apr. 30, 2015 (SE) .................................... 1550536-5

(51) Int. Cl.
*A61B 17/32* (2006.01)
*A61B 17/22* (2006.01)
*A61B 17/3207* (2006.01)

(52) U.S. Cl.
CPC ...... *A61B 17/320016* (2013.01); *A61B 17/22* (2013.01); *A61B 17/3207* (2013.01);
(Continued)

(58) Field of Classification Search
CPC ............ A61B 17/320016; A61B 17/22; A61B 17/3207; A61B 17/320783;
(Continued)

(56) References Cited

U.S. PATENT DOCUMENTS 4,024,869 A 5/1977 Bonnet
4,538,610 A 9/1985 Kubota
(Continued)

FOREIGN PATENT DOCUMENTS

EP 1980220 A1 10/2008
EP 2095773 A1 9/2009
(Continued)

OTHER PUBLICATIONS

Hologic, MyoSure Tissue Removal System, 2014.

*Primary Examiner* — Jocelin C Tanner
(74) *Attorney, Agent, or Firm* — Dinsmore & Shohl LLP

(57) ABSTRACT

The present disclosure relates to a tissue cutting system for cutting tissue of a heart, such as tissue of a septum of a heart, comprising: an outer tubular member having a proximal portion and a distal portion, said distal portion comprising a tissue resection window; a resection element axially slidably arranged inside the outer tubular member configured to resect tissue extending through the tissue resection window; at least one pressure sensor; wherein the outer tubular member and resection element are arranged to establish: a first fluid flow channel suitable for transporting resected tissue away from an area adjacent to the resection element; at least one second fluid flow channel configured to assist the first fluid flow channel in transporting resected tissue. The present disclosure further relates to a method for resecting tissue using the disclosed tissue cutting system.

10 Claims, 12 Drawing Sheets

(52) U.S. Cl.
CPC ............. *A61B 17/320783* (2013.01); *A61B 2017/320028* (2013.01)

(58) Field of Classification Search
CPC ........ A61B 17/3205; A61B 17/320725; A61B 17/320758; A61B 2017/320028
See application file for complete search history.

(56) References Cited

U.S. PATENT DOCUMENTS

| | | | |
|---|---|---|---|
| 5,088,998 | A | 2/1992 | Sakashita et al. |
| 5,411,552 | A | 5/1995 | Andersen et al. |
| 5,855,601 | A | 1/1999 | Bessler et al. |
| 5,928,218 | A | 7/1999 | Gelbfish |
| 6,152,919 | A | 11/2000 | Hakky |
| 6,231,518 | B1 | 5/2001 | Grabek et al. |
| 6,343,605 | B1 | 2/2002 | Lafontaine |
| 6,485,500 | B1 | 11/2002 | Kokish et al. |
| 6,824,544 | B2 | 11/2004 | Boebel et al. |
| 6,893,441 | B2 | 5/2005 | Brommersma et al. |
| 7,125,414 | B2 | 10/2006 | Blackledge et al. |
| 7,323,002 | B2 | 1/2008 | Johnson et al. |
| 7,338,467 | B2 | 3/2008 | Lutter |
| 7,585,321 | B2 | 9/2009 | Cribier |
| 7,674,238 | B2 | 3/2010 | Weber et al. |
| 7,699,866 | B2 | 4/2010 | Bates et al. |
| 7,766,936 | B2 | 8/2010 | Ladd |
| 7,892,281 | B2 | 2/2011 | Seguin et al. |
| 7,959,666 | B2 | 6/2011 | Salahieh et al. |
| 8,092,521 | B2 | 1/2012 | Figulla et al. |
| 8,231,544 | B2 | 7/2012 | Mark |
| 8,236,024 | B2 | 8/2012 | Stanford et al. |
| 10,610,249 | B2* | 4/2020 | Bjursten ............ A61B 17/3207 |
| 2003/0040764 | A1* | 2/2003 | Adams ........... A61B 17/320016 606/170 |
| 2004/0049128 | A1 | 3/2004 | Miller et al. |
| 2004/0167554 | A1 | 8/2004 | Simpson et al. |
| 2007/0276352 | A1 | 11/2007 | Crocker et al. |
| 2009/0270898 | A1 | 10/2009 | Chin et al. |
| 2010/0081964 | A1* | 4/2010 | Mark ................. A61B 10/0283 600/566 |
| 2011/0208256 | A1* | 8/2011 | Zuhars ............... A61F 2/30942 606/86 R |
| 2011/0306995 | A1 | 12/2011 | Moberg |
| 2012/0283824 | A1 | 11/2012 | Lutter et al. |
| 2013/0046316 | A1* | 2/2013 | Sullivan ............... A61M 1/7411 606/115 |
| 2013/0345551 | A1* | 12/2013 | Arts ...................... A61B 18/14 606/41 |
| 2014/0031834 | A1* | 1/2014 | Germain ................ A61B 1/303 606/119 |
| 2014/0290649 | A1* | 10/2014 | Maguire ......... A61M 16/0443 128/202.16 |
| 2015/0105791 | A1* | 4/2015 | Truckai .......... A61B 17/320068 606/115 |
| 2015/0265302 | A1* | 9/2015 | Wilson .................... A61B 8/12 606/190 |

FOREIGN PATENT DOCUMENTS

| | | |
|---|---|---|
| WO | 2013110073 A1 | 7/2013 |
| WO | 2014028366 A1 | 2/2014 |

* cited by examiner

TISSUE CUTTING DEVICE AND SYSTEM

REFERENCE TO RELATED APPLICATIONS

This application is a continuation of U.S. patent application Ser. No. 15/570,451, filed Oct. 30, 2017, which is a U.S. national phase of PCT/EP2016/059590, filed Apr. 29, 2016, which claims priority from Sweden Patent Application 1550536-5, filed Apr. 30, 2015. The entire content of each application is incorporated herein by reference.

FIELD OF THE INVENTION

The present disclosure relates to a tissue cutting device, a tissue cutting system and to a method for resecting tissue.

BACKGROUND OF THE INVENTION

Heart disease is the most common chronic disease in the developed world, and quickly increasing the developing world. It is responsible of 16% of the deaths in high income countries and 14% in middle income countries as defined by the World Health Organization. Ischemic heart disease is the most common for mortality, with valvular disease in the second place. Between 2% and 4% of the population over 65 is estimated to have some type of valvular disease. The most common valvular disease is the aortic stenosis, followed by mitral stenosis and mitral regurgitation. Another condition that is not uncommon is subvalvular stenosis due to hypertrophy of the septum (106), where there is an obstruction below the aortic valve that affect the heart in the same way as the aortic stenosis does (FIGS. 1A and 1B). Subvalvular stenosis increases the work needed for the heart to maintain the blood pressure and cardiac output. When severe, the condition decreases cardiac output with decreased physical strength as a consequence. In addition, the condition increases the likelihood of dying prematurely in heart failure.

Septal hypertrophy is the medical term used when the septum dividing the right and left ventricle of the heart is hypertrophic, i.e. thicker than normally. This thickening will lead to an obstruction in the outflow of the left ventricle. The pathogenesis of septal hypertrophy is mainly twofold. First it could be a part of a hypertrophic cardiomyopathy, where the entire muscle mass of the heart is increased. The second cause is secondary to an aortic stenosis, where the stenosis of the valve leads to an increase in work load and increase in the muscle mass of the septum. In both these conditions, the thickness of the septum (106) increases from a normal 6-10 mm to up to 25-30 mm. The thickest part is just below in the aortic valve in the tubular part of the left ventricle (103) called the outflow tract (104) (FIG. 1*b*). As the septum (106) bulges into this tubular part, an obstruction will develop in the part where the blood normally is ejected to the circulation.

Currently, the treatment modalities available for septal hypertrophy are 1) surgical myectomi, 2) Alcohol Septal Ablataion (ASA) and 3) dual chamber pace-maker pacing.

Surgical myectomi is done by routine open heart surgery, where the chest is opened by a median sternotomy, the patient is put on heart-lung machine and the heart is arrested. When cardiopulmonary bypass is instituted, the surgeon can open the heart and resect a part of the hypertrophic septum. Alcohol septal ablation is performed by instilling alcohol in the coronary arteries that supplies the septum with blood. The procedure is performed in a catheter lab with the patient awake, and through routine access in the groin. The alcohol will trigger a cell death and necrosis, and thereby decreasing the volume of the septum. Pace-maker therapy is performed to achieve a contraction pattern of the septum that will decrease the outflow obstruction.

All of the above treatment modalities are associated with inconveniences. Surgical myectomi is invasive and can be considered a relatively complicated surgical process involving substantial risks for the patent undergoing the surgery since the chest has to be opened and the heart arrested. ASA and pace-maker therapy can be considered to be selective alternatives for certain cases of e.g. lighter forms of septal hypertrophy in cases where surgical myectomi is not suitable for the patient. The above described techniques for treating septal hypertrophy both have the same disadvantage in that it is difficult to control the amount of septum to remove. Surgical resection depends on the experience of the surgeon to remove the right amount of tissue. If the surgeon removes too much tissue there will be a defect in the septum, in if the surgeon removes too little the patient will not be entirely cured. For ASA the achieved effect is difficult to control as the operator does not know how much of the septum that will go into necrosis.

SUMMARY OF THE INVENTION

Heart surgery without arresting the heart, in particular involving resection of a part of the hypertrophic septum, presents several challenges that are not overcome by traditional tissue cutting devices. First of all, when performing surgery on a beating heart, the interior of the heart is filled with blood, i.e. the surgery (tissue cutting) is performed in the blood circulation. It is of importance that substantially no blood should be aspirated from the heart or blood circulation during the surgery, nor should substantially no fluids be added to the blood circulation from the device or anything belonging to the system of the device.

Furthermore, when working on a beating heart, the pressure in the blood in the heart chambers varies, both within one cardiac cycle and over several cardiac cycles, which varies the relative pressure between a transportation channel of a tissue cutting device and the external environment in which it operates accordingly.

Yet another issue when performing surgery in the blood circulation, as compared to other organs of the body, is that no resected tissue should be allowed to be released into the blood circulation in order to avoid embolic events, thrombosis or the like.

The present disclosure relates to a tissue cutting system for cutting tissue of a heart, such as tissue of a septum of a heart, comprising: an outer tubular member having a proximal portion and a distal portion, said distal portion comprising a tissue resection window; a resection element axially slidably arranged inside the outer tubular member configured to resect tissue extending through the tissue resection window; at least one pressure sensor; wherein the outer tubular member and resection element are arranged to establish: a first fluid flow channel suitable for transporting resected tissue away from an area adjacent to the resection element; at least one second fluid flow channel configured to assist the first fluid flow channel in transporting resected tissue.

A tissue cutting system according to the present invention can be seen as a tool to resect tissue in a controlled manner with reduced invasiveness. This can be achieved by a device having an outer tubular member and an internal cutting mechanism which is slidably arranged inside the outer tubular member. To cut and remove tissue the device is held close to the tissue to be resected, while the resection window is open. By aspirating through the first fluid flow channel, tissue is aspirated through the resection window, thereby extending through the tissue resection window. While the tissue extends through the resection window, the resection element can be moved across the resection window along the axis of the outer tubular outer member to resect the tissue extending through the resection window. Once the tissue is resected it can be transported away from the resection element through the first fluid flow channel. In addition to the first fluid flow channel there is at least one second fluid flow channel. The at least one second fluid flow channel is typically but not necessarily located between the outer tubular member and inner tubular member. The second fluid flow channel can generally be said to regulate a pressure in the tissue cutting device, and more specifically in the distal portion. In one embodiment the step of regulating a pressure comprises the step of maintaining equilibrium in relation to the pressure outside the device when the resection window is open. In one embodiment the step of regulating a pressure comprises the step of increasing the pressure in the second fluid flow channel, thereby applying liquid to a region adjacent to the resection window, where tissue is cut, thereby assisting the first fluid flow channel in transporting resected tissue away from the resection element.

The present invention may further comprise any of the following features: a vacuum generator; a collector for collecting the resected tissue; an actuator for controlling a sliding movement of the resection element along the outer tubular member; and a housing. In one embodiment the tissue cutting system is a complete system for removing tissue. In one embodiment, the tissue cutting system is configured to resect a hypertrophic septum of a heart, and therefore, accordingly, the tissue cutting system is a device suitable for resecting and removing tissue of a hypertrophic septum of a heart.

A further aspect of the presently disclosed invention relates to a method for resecting tissue using a tissue cutting system as described above. The method presents a major advantage compared to for example surgical myectomi in that the method is considerably less invasive. In one embodiment the method also gives a continuous monitoring of how much tissue has been resected, giving the operator feed-back as when to continue or stop resecting. This can be achieved by continuous monitoring by echocardiography of the heart (either as a transeosophagel echocardiography or transthoracic echocardiography). A continuous monitoring of the systolic and diastolic pressure in the right ventricle through the instrument together with continuous monitoring of the arterial pressure will give a measure of the degree of outflow obstruction, and the treatment effect which can also be used to guide the effectiveness of the procedure. The method comprises the steps of: positioning the resection window adjacent to tissue to cut; generating a vacuum pressure; connecting the vacuum pressure to the first fluid flow channel, thereby aspirating tissue through the resection window; measuring and analysing the pressure in the first fluid channel for a predefined period of time; and if the measured period remains below a predefined pressure threshold for longer than a predefine period of time, sliding the resection element thereby cutting tissue, otherwise disconnecting the vacuum pressure to the first fluid flow channel. The steps may be iteratively repeated. The presently disclosed tissue cutting system provides a possibility to cut tissue in a heart while preventing unnecessary aspiration of blood from the heart. When the vacuum pressure is connected, e.g. by opening a valve, it will quickly be realized whether the resection window is filled with tissue without leakage. If the pressure remains low for a predefined period of time, it is considered that the device has been positioned such that the vacuum is able to "grip" the tissue without leakage and the cutting can be done. If the pressure in the first fluid flow channel remains low only temporarily and then goes back to a higher level, it can be used as an indication that the generated the resection window has not "gripped" the tissue and the vacuum pressure must therefore be disconnected in order to avoid aspiration of blood.

Alternatively the method comprises the steps of: opening the tissue resection window and during and after the opening regulating the pressure in the distal portion through the at least one second fluid flow channel such that the pressure is substantially equal to the pressure outside the tissue cutting system; activate a vacuum generator connected to the first fluid flow channel such that tissue located outside the cutting system is aspirated into the distal portion of the outer tubular member through the tissue resection window; closing the tissue resection window by sliding the inner tubular member in an axial direction lengthwise of the outer tubular member towards the closed distal end, the resection element thereby resecting tissue extending through the tissue resection window; increasing the pressure in the outer channel to generate a flow of liquid through the outer channel towards the distal portion, the flow of liquid continuing from the distal portion away from the distal portion through the first fluid flow channel. The inventor has realized that by using a second fluid flow channel to balance the pressure in the distal portion adjacent to the resection window with a pressure outside the device the device can used invasively since the equilibrium in relation to the pressure outside the device prevents that material moves between the outside and the inside of the device. Before the vacuum generator is activated in the second step, the resection window should preferably be located adjacent to or directly against the tissue to be resected. The vacuum generator is then activated, preferably decreasing the pressure in the cutting device rapidly, and tissue is aspirated into the distal portion of the outer tubular member through the tissue resection window. The inner tubular member is then slid inside the outer tubular member, thereby closing the resection window and cutting tissue. At approximately the same time or slightly after the pressure in the second fluid flow channel is increased to generate a flow of liquid through the outer channel towards the distal portion, thereby assisting in transporting tissue away from the cutting element.

These and other aspects of the invention are set forth in the following detailed description if the invention.

BRIEF DESCRIPTION OF THE DRAWINGS

The invention will in the following be described in greater detail with reference to the accompanying drawings. The drawings are exemplary and are intended to illustrate some of the features of the presently disclosed tissue cutting system, and are not to be construed as limiting to the presently disclosed invention.

FIG. 1A shows a transection of a normal heart. FIG. 1B shows a transection of a heart having a hypertrophic septum;

FIG. 2A shows an untreated heart and FIG. 2B shows a heart where tissue has been removed from the septal part;

In FIG. 3A the resection window is closed and in FIG. 3B the resection window is open;

DETAILED DESCRIPTION OF THE INVENTION

The present disclosure relates to a tissue cutting system for cutting tissue of a heart, such as tissue of a septum of a heart, comprising: an outer tubular member having a proximal portion and a distal portion, said distal portion comprising a tissue resection window; a resection element axially slidably arranged inside the outer tubular member configured to resect tissue extending through the tissue resection window, and at least one pressure sensor wherein the outer tubular member and the resection element are arranged to establish: a first fluid flow channel suitable for transporting resected tissue away from an area adjacent to the resection element; at least one second fluid flow channel configured to assist the first fluid flow channel in transporting resected tissue. The device may be a transcatheter device designed to resect tissue, such as parts of the septum, in a controlled manner with a minimal invasive approach.

Figure 3A:
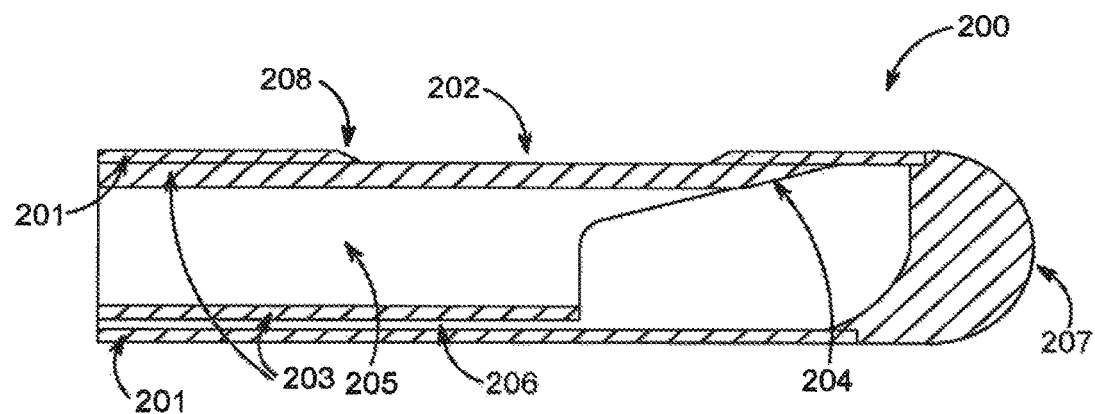
FIGS. 3A-3B show an embodiment of the tissue cutting system.
Figure 3B:
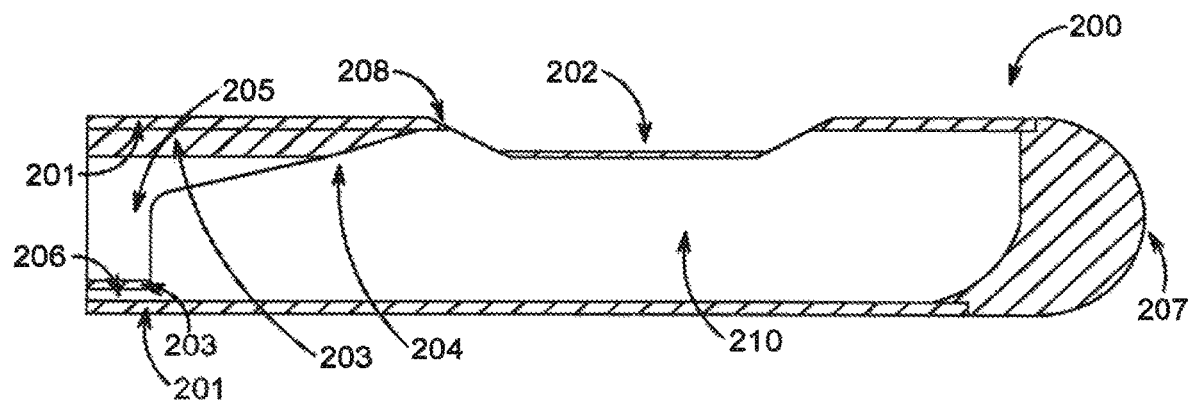

The system may further comprise an inner tubular member axially slidably arranged inside the outer tubular member. The outer and inner tubular members are preferably rigid. The inner tubular member being axially slidably arranged inside the outer tubular member means that it can be moved in the longitudinal direction of the outer tubular member. FIGS. 3A and 3B show one embodiment of the device, in which the inner tubular member (203) is located at different positions in relation to the outer tubular member (201). The outer tubular member having a resection window refers to an opening through which tissue can extend, typically by means of aspiration. The distal portion of the outer tubular member refers to the part of the tubular member being location adjacent to the resection window and the proximal accordingly to the opposite part of the outer tubular member. The device further comprises a resection element configured to resect tissue extending through the tissue resection window. This means that the resection element is configured to slide across the resection window parallel to the sidewall of the outer tubular member to shear tissue that is located inside the outer tubular member. Typically the resection element is an integrated part of the inner tubular member.

'Tubular' in inner and outer tubular members is to be construed broadly and includes pipes and cylinders having any suitable cross-section that is substantially circular, oval, rounded, square, rectangular or other shape, which would be known to those skilled in the art.

The inner and outer tubular members are arranged to establish a first fluid flow channel suitable for transporting resected tissue away from an area adjacent to the resection element, and at least one second fluid flow channel suitable for regulating a pressure in the distal portion and/or configured to assist the first fluid flow channel in transporting resected tissue. This design allows that the device is connected to a vacuum generator (more specifically that the first fluid flow channel, which may be the interior of the inner tubular member, is connected to a vacuum generator), and when the vacuum generator is activated the resected tissue is aspirated away from the area in the distal portion of the outer tubular member adjacent to the resection window. 'Vacuum' may generally be referred to a pressure much less than atmospheric pressure. In relation to the present invention, 'vacuum' is construed broadly as an at least partial vacuum (imperfect vacuum) with the intention that a pressure in the first fluid flow channel that is negative in relation to the pressure outside the resection window can be used to aspirate tissue into the first fluid flow channel, and, after being cut, further through the first fluid flow channel. The at least one second fluid flow channel may have different purposes, which can broadly be described as regulating a pressure in the distal portion and/or assisting the first fluid flow channel in transporting resected tissue. More specifically this means that when the resection window is open, the outside of the device and the inside of the device is in fluid connection. To prevent that material moves from the outside to the inside or vice versa the second fluid flow channel can regulate the pressure such that equilibrium is maintained, i.e. the pressure is substantially the same inside and outside the device. When the resection window is closed the second fluid flow channel can be used to assist the first fluid channel in transporting resected tissue away from the distal part through the first fluid channel. This may be achieved by increasing the pressure of a liquid connected to the second fluid flow channel. As a consequence, the liquid flows through the second fluid flow channel towards the distal portion of the device, where resected tissue is flushes away through the first fluid flow channel.

Resection Window

The resection device of the tissue cutting system may have different dimensions, location and design depending on the tissue to cut, the dimensions of the inner and outer tubular members, the performance of a vacuum generator connected to the device etc.

When used invasively there may be physical constraints that have to be taken into account. One such constraint is related to the limited space around the septum of a heart. Therefore, one aspect of the presently disclosed tissue cutting device relates to the resection window being located sufficiently close to a closed distal end of the outer tubular member that the device can be positioned close to the tissue to be resected without damaging other surrounding parts. Therefore, the resection window may be located proximate to a closed distal end of the outer tubular member, such as less than 0.1 mm, or less than 0.2 mm, or less than 0.3 mm, or less than 0.4 mm, or less than 0.5 mm, or less than 1.0 mm, or less than 2.0 mm, or less than 3.0 mm, or less than 4.0 mm, or less than 5.0 mm, or less than 10 mm, or less than 15 mm, or less than 20 mm, or less than 25 mm, or less than 30 mm.

As stated, the dimensions and the shape of the resection window depend on a number of factors. The resection window may have a length of less than 3 mm, or less than 4 mm, or less than 5 mm, or less than 6 mm, or less than 7 mm, or less than 8 mm, or less than 9 mm, or less than 10 mm, or less than 15 mm, or less than 20 mm, or less than 25 mm, or less than 30 mm, or less than 50 mm. Length is defined as the distance of the resection window in the longitudinal direction of the outer tubular member. If the device is used to resect the hypertrophic septum of a heart, the size of the window preferably has a size that supports a safe and secure resection of small tissue parts. It will in most situations be preferred that septum resection is performed through several cuts, optionally in a session supported by e.g. transoesophageal or transthoracic echocardiography of the heart and/or fluoroscopy, wherein tissue parts are resected and removed repeatedly while the result (i.e. the size and shape of the septum after removal of tissue) is continuously checked. On the other hand, the larger pieces of tissue that can be resected per cut, the faster the process. Hence, the length of the window is a trade-off between precision/granularity and speed/efficiency.

Further different shapes of the resection are possible. Preferably the curvature of the edge of the resection window is substantially smooth, and may have a substantially oval shape. If the cross-section of the outer tubular member is rounded or substantially circular, the resection window typically extends over of portion of a circumference of the outer tubular member. The resection window may extend over a portion of a circumference of the outer tubular member, such as less than 5% of the circumference, or less than 6% of the circumference, or less than 7% of the circumference, or less than 8% of the circumference, or less than 9% of the circumference, or less than 10% of the circumference, or less than 15% of the circumference, or less than 20% of the circumference, or less than 30% of the circumference, or less than 40% of the circumference, or less than 50% of the circumference, or less than 60% of the circumference.

Figure 4A:
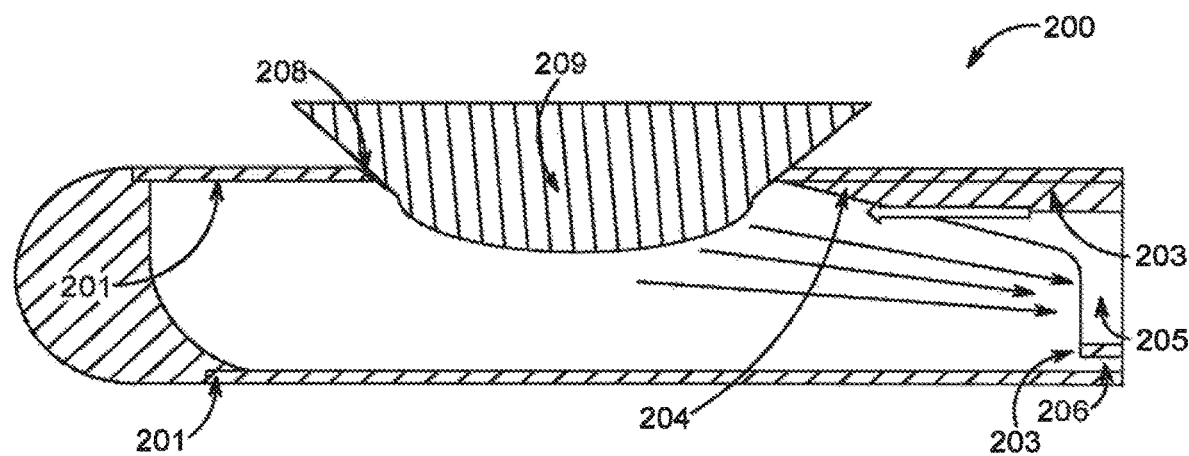
FIGS. 4A-4B show another embodiment of the tissue cutting system. The figures illustrate how tissue is aspirated into the distal portion of the device and transported away from the resection element through the first fluid flow channel.
Figure 4B:
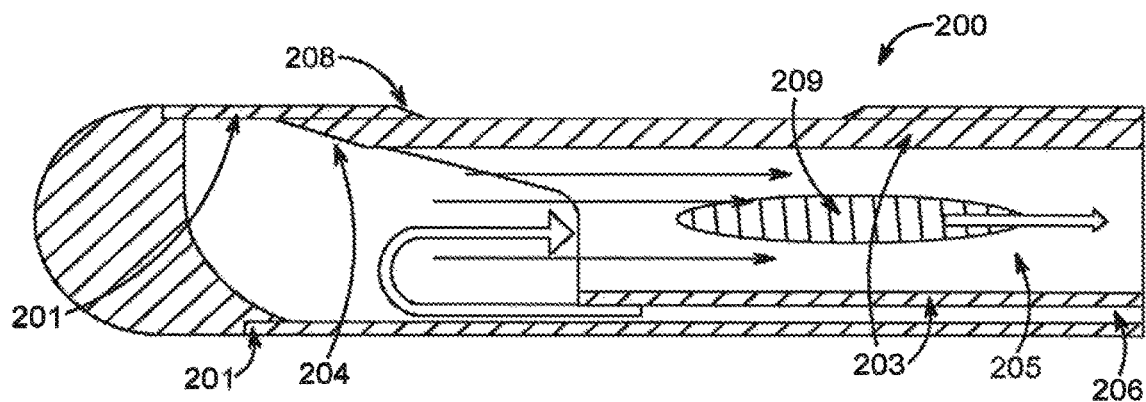

One embodiment of the presently disclosed invention relates to the resection window having an edge sloping downwards towards the center of the resection window. An example of a resection window (202) having a sloping edge (208) can be seen in FIGS. 3A-3B. Such a sloping edge can be said to correspond to one of the blades of a pair of scissors. This is a common design of the cutting edges of scissors. The edge of the resection window can be said to correspond to one of the blades of a pair of scissors in this regard. The other blade corresponds to the resection element of the present invention. When the resection element (204), which is an integral part of inner tubular member (203) in the tissue cutting device in FIGS. 3A-3B, slides across the resection window, tissue (209) extending through the resection window is resected, as illustrated in FIGS. 4A-4B.

Resection Element

The resection element according to the present invention can take different forms. The functionality can generally be said to be similar to that of scissors, i.e. two parallel blades sliding and when the edges meet the material that is between the two edges is sheared. In the present invention the resection element can be said to correspond to one of the blades of a pair of scissors (the other blade corresponding to the edge of the resection window, as explained above). However, this illustration shall not be seen as limiting in the sense that the resection does not have to be a flat surface as the blade of scissors.

Figure 14:
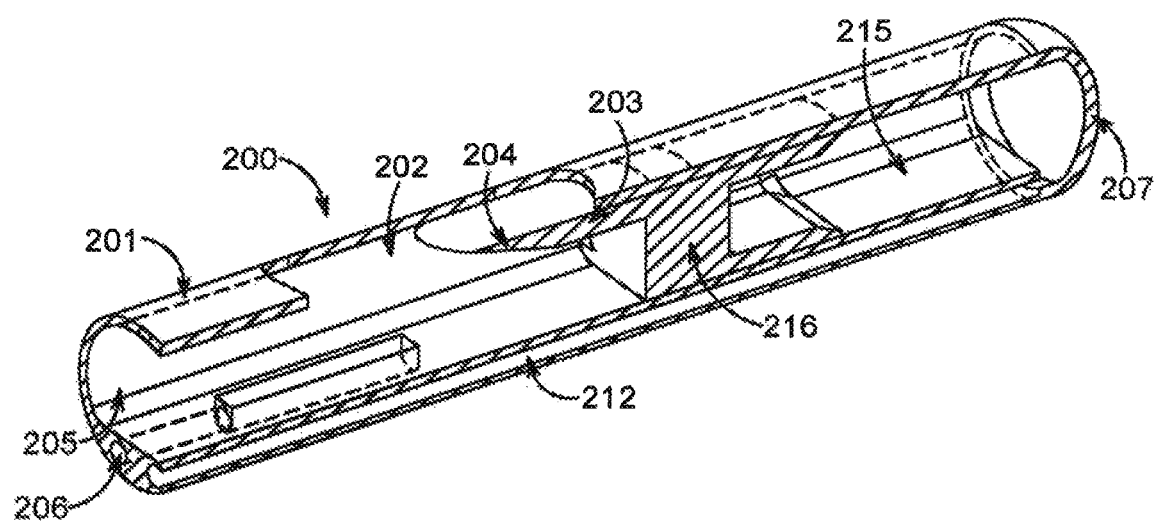
FIG. 14 shows a further embodiment of the tissue cutting system having a backwardly cutting resection element.

In one embodiment the resection element is configured to cut tissue backwards towards a direction from the distal portion towards the proximal portion. This may be achieved by having the resection element located distally to the resection window when the resection window is open. FIG. 14 shows such an implementation. The resection element may be directly connected to or forming an integral part of a plunger sealingly engaged inside the outer tubular member, as shown in FIG. 14. The plunger and outer tubular member may form a chamber which can be used to push or retract the resection element by regulating the pressure inside the chamber. This embodiment is particularly useful if the tissue cutting device is connected through for example a plastic catheter since it enables a possibility to control the resection element through a fluidly connected element by regulating for example the pressure of a fluid rather than a rigidly connected mechanism.

In relation to such an embodiment a resection element control channel may be incorporated into the sidewall of the outer tubular member, wherein the resection element control channel is in fluid connection with a closed chamber defined by the outer tubular member and the plunger. The system may be configured to control a fluid in the closed chamber such that when a chamber pressure in the chamber is increased a backwards movement of the resection element is produced and when the chamber pressure is decreased a forwards movement of the resection element is produced.

Further options for controlling the resection element may include the use of a wire and/or a substantially rigid mechanical connection between the control device and the resection element. The connection between the control device and the resection element may be driven by a motor, for example an electrical motor.

Figure 7A:
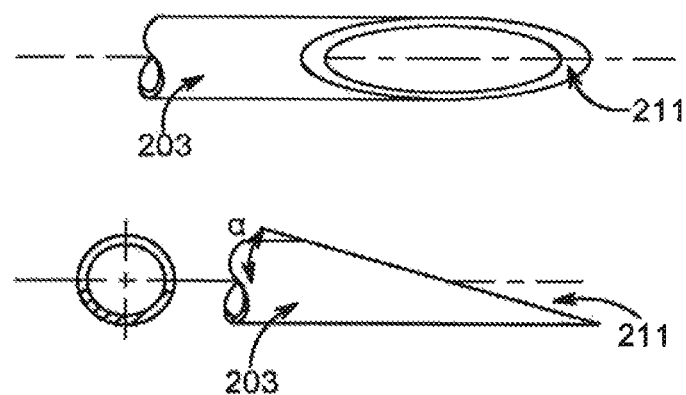
FIGS. 7A-7C show three different resection elements.
Figure 7B:
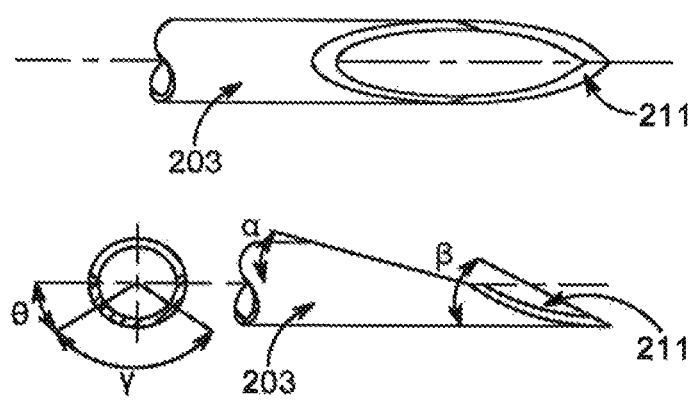
Figure 7C:
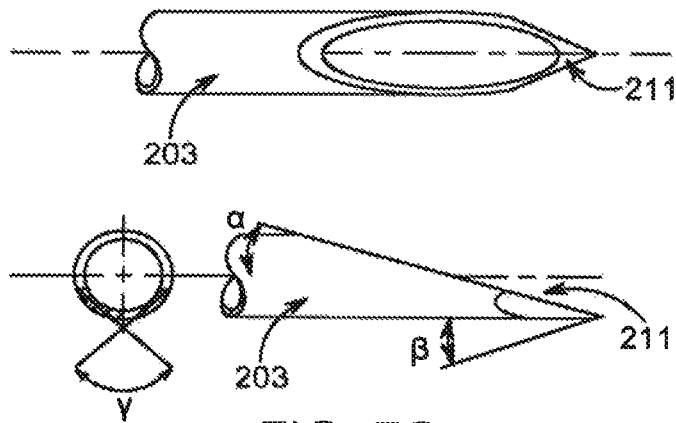

In one embodiment, the resection element is an integrated part of the inner tubular member. Therefore, in one embodiment of the invention the inner tubular member has a hollow interior defining the first fluid flow channel extending from an open proximal end of the inner tubular member to an open distal end of the inner tubular member, said open distal end comprising a cutting surface defining an acute angle to the longitudinal axis of the inner tubular member, forming a substantially oval edge of the inner tubular member. Examples of such embodiments are shown in FIGS. 7A-7C. The open distal end shall in this context be construed as the end which is located adjacent to the distal portion of the outer tubular member, i.e. where the resection window is located. The open proximal end shall be construed as the opposite end of the inner tubular member, possibly configured to be connected to a vacuum generator. Alternatively, the inner tubular member can be said to be a tissue penetrating cannula, wherein the open distal end is sharp.

From the above explanations it can be noted that the resection element may be either substantially flat, or, if it is regarded as an extension of the inner tubular member, having a substantially round cross-section following the contour of the inside of the outer tubular member. Besides resecting tissue extending through the resection window, the resection element should preferably be able to seal the resection window when it has been slid across the resection window, i.e. act as a barrier between the inside and the outside of the device such that no material can flow between the inside and the outside. In one embodiment, an upper side of the resection element is configured to slide smoothly along the inside of the outer tubular member, thereby cutting tissue extending through the tissue resection window. This design seals the resection window efficiently.

Different shapes of the resection elements are possible both in terms of the cutting edge of the inner tubular member (if the resection element is an integral part of the inner tubular member) and the acute angle. FIGS. 7A-7C show a number of examples of shapes. In one embodiment the cannula is a lancet cannula having a sharpened front, and in one embodiment the acute angle is between 1° and 30° and in another embodiment the open distal end of the inner tubular member comprises a scalpel or razor blade.

Configuration of Outer and Inner Tubular Members, and Fluid Flow Channels

As stated the tissue cutting system has an outer tubular member with a resection window, optionally an inner tubular member, and a resection element configured to resect tissue extending through the tissue resection window. The tubular members are arranged to establish a first fluid flow channel and at least one second fluid flow channel.

In one embodiment the first fluid channel is defined as the hollow interior of the inner tubular member. The at least one second fluid flow channel can be a space between the outer tubular member and the inner tubular member. In FIG. 3A, showing one embodiment of the presently disclosed invention, it can be seen that the upper side of the inner tubular is located directly against the inside of the outer tubular member (201). Upper side in this context shall be construed as the side of tube closest to the resection window (202). In this embodiment the second fluid flow channel (206) is located in the opposite side of a cross-section of the outer tubular member in relation to the resection window (202). The first fluid flow channel (205) is the hollow interior of the inner tubular member (203) in this example. The second fluid flow channel (206) in FIG. 3A is located in the lower section of the outer tubular member (201), between the inner tubular member (203) and the outer tubular member (201). FIG. 4B shows a similar configuration, which illustrates how resected tissue (209) is transported away from the area adjacent to the resection element (204) through the first fluid flow channel (205).

The at least one second fluid flow channel does not necessarily have to be located between the outer tubular member and the inner tubular member. If any of the sidewalls of the tubular members are sufficiently thick, the at least one second fluid flow channel may be incorporated into the sidewalls of the tubular members. Alternatively, in one embodiment the cutting device has one or more additional fluid flow channels on the outside of the device, either attached on the outside of the device or as separate channels. A consequence of such a configuration is that the device further comprises at least one additional tubular member outside the outer tubular member. Possibly, the device also comprises an additional tubular member inside the inner tubular member.

In one embodiment, the cutting device has a device outer diameter between 2 mm and 20 mm, or between 2 mm and 15 mm, or between 2 mm and 10 mm, or between 5 mm and 10 mm, or between 5 mm and 15 mm, such as 2 mm, or 3 mm, or 4 mm, or 5 mm, or 6 mm, or 7 mm, or 8 mm, or 9 mm, or 10 mm, or 11 mm, or 12 mm, or 13 mm, or 14 mm, or 15 mm, or 16 mm, or 17 mm, or 18 mm, or 19 mm, or 20 mm. When used as a device for resecting the hypertrophic septum of a human or animal heart, this outer diameter ensures that the device is sufficiently small to be inserted into the body through the apex of the heart via an intercostal space or through the vasculature of the body, and at the same time sufficiently large to cut as large pieces of tissue as possible.

The inner tubular inner diameter can be said to define an upper limit of the pieces of tissue that can be transported (in the case where the interior of the inner tubular member defines the first fluid channel). In one embodiment the inner tubular member has an inner tubular inner diameter between 1 mm and 10 mm, or between 1 mm and 7 mm, or between 1 mm and 5 mm, or between 1 mm and 3 mm, such as 1 mm, or 2 mm, or 3 mm, or 4 mm, or 5 mm, or 6 mm, or 7 mm, or 8 mm, or 9 mm, or 10 mm, or 12 mm, or 14 mm, or 16 mm, or 18 mm, or 19 mm.

In the case where the at least one second fluid flow channel is a space between the outer tubular member and the inner tubular member, the difference between an inner tubular outer diameter of the inner tubular member and an outer tubular inner diameter can be said to define the width of the second fluid flow channel. The difference between an inner tubular outer diameter of the inner tubular member and an outer tubular inner diameter can be less than 5 mm, or less than 4 mm, or less than 3 mm, or less than 2 mm, or less than 1 mm, or less than 0.5 mm, or less than 0.4 mm, or less than 0.3 mm, or less than 0.2 mm, or less than 0.1 mm.

The length of the device can be seen as the distance between the distal end and the proximal end of the outer tubular. The lower limit of the device is preferably such that the device extends from the point where it operates, typically adjacent to the hypertrophic septum of a heart, to the outside of an area of critical tissue, organ or any other body function, e.g. beyond the apex of the heart. In one embodiment the tissue cutting device has a length of less than 30 mm, or less than 40 mm, or less than 50 mm, or less than 60 mm, or less than 70 mm, or less than 80 mm, or less than 90 mm, or less than 100 mm. There is no upper limit of this length—the device can in principle operate both as a short device and a long device. Nevertheless, in one embodiment the tissue cutting device has a length of between 50 mm and 500 mm, or between 50 mm and 400 mm, or between 100 mm and 300 mm, or between 50 mm and 200 mm, or between 100 mm and 200 mm, or greater than 200 mm.

In another embodiment of the invention the cutting device is configured for use through the femoral artery, the ascending aorta, subclavian artery or any other great vessel of the body. Great vessels is a term used to refer collectively to the large vessels that bring blood to and from the heart, including the venae cavae, pulmonary artery, pulmonary veins and aorta, and can in relation to the present invention be construed as any vessel through which the cutting device can pass. In this embodiment the tissue cutting device preferably further comprises a flexible section attached to the device configured to pass through any great vessel of the body, including for instance the aortic arch. In one embodiment the flexible section has a length of between 50 mm and 1000 mm, or between 50 mm and 500 mm, or between 100 mm and 300 mm, or between 50 mm and 200 mm, or between 100 mm and 200 mm, or greater than 200 mm, such as 50 mm, or 60 mm, or 70 mm, or 80 mm, or 90 mm, or 100 mm, or 150 mm, or 200 mm, or 300 mm, or 400 mm, or 500 mm, or 600 mm, or 700 mm, or 800 mm, or 900 mm, or 1000 mm.

In one embodiment the tissue cutting device further comprises a guidewire to guide the tissue cutting device to a position inside the body. A guidewire is a usually flexible wire that can be inserted to a space to act as a guide for subsequent insertion of a stiffer or bulkier instrument. Cardiovascular interventional guidewires are known to those skilled in the art. The guidewire is placed in one of the channels of the cutting device and can track its way to the correct position for the device to operate. Typically the guidewire is introduced before the rest of the device through the access site (e.g. apex, femoral artery, ascending aorta, subclavian etc.). In one embodiment the tissue cutting system further comprises a guidewire channel incorporated into the sidewall of the outer tubular member. A guidewire incorporated in this manner may be useful for example if the tool is to be used by accessing the heart transfemorally. In one embodiment the system therefore further comprises a guidewire arranged inside the guidewire channel extending from a proximal end of the outer tubal member to a distal end of the outer tubular member.

In another embodiment the tissue cutting device further comprises an introducer configured to introduce the tissue cutting device into any part or organ of the body, such as the heart. Introducers are known in the art and are used to provide access to the heart. Introducers may comprise means for puncturing tissue and means for providing access to the interior of the heart.

Preferably, the tissue cutting device is made of a rigid material selected from the group of ceramics, ceramic composites, metal, such as aluminium or steel, or plastics, such as polycarbonate (PC) or polymethylmethacrylate (PMMA).

Functional Description

As stated, the fluid flow channels of the present invention are configured to perform different functional tasks; the first fluid flow channel is suitable for transporting resected tissue away from an area adjacent to the resection element, and the at least one second fluid flow channel is/are suitable for regulating a pressure in the distal portion and/or assist the first fluid flow channel in transporting resected tissue. More specifically, the first fluid flow does not transport the resected tissue by itself but typically by a device aspirating the tissue through the channel. Therefore, in one embodiment the first fluid flow channel is configured to be connected to a vacuum source configured to establish a fluid flow to aspirate resected tissue away from an area adjacent to the resection element through the channel. This typically happens when the resection element has been slid forward, thereby resecting tissue extending through the resection window, such that there are loose tissue parts in the distal portion of the outer tubular member. Typically, the tissue is transported away from the resection element by means of aspiration. The term vacuum generator shall be construed broadly as any device capable of generating a negative pressure in relation to a given starting point pressure. Vacuum in this sense does not necessarily mean absolute vacuum, but includes partial vacuum, i.e. any negative pressure between the original pressure and absolute vacuum.

Figure 12:
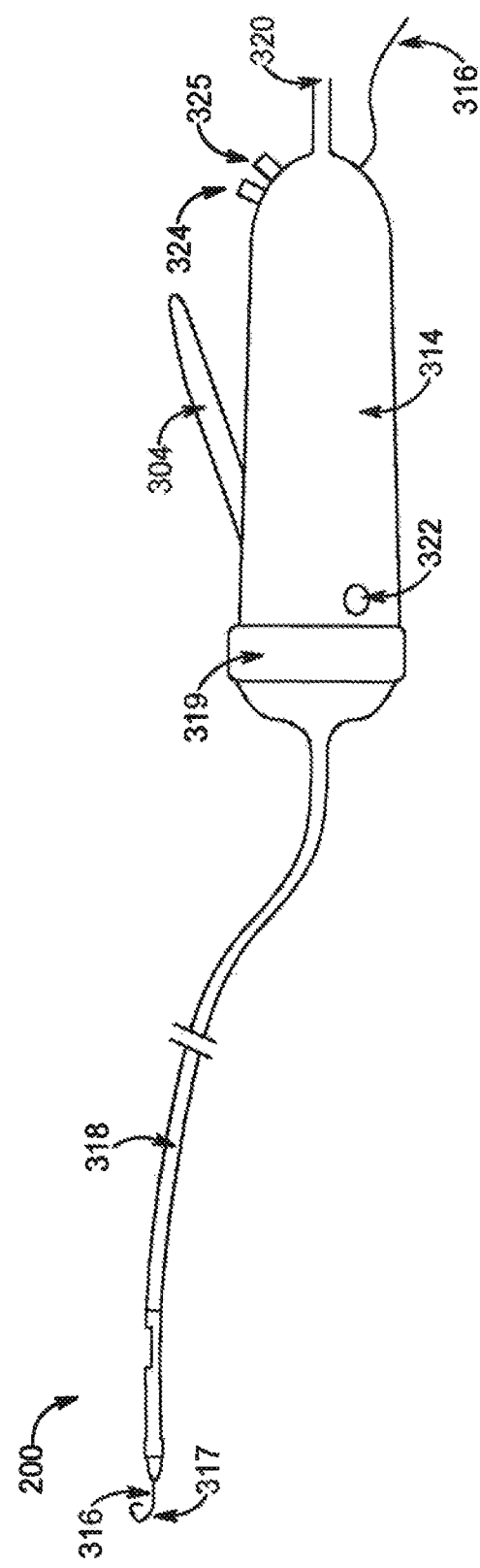
FIG. 12 shows one embodiment of the tissue cutting system having a catheter and a control device.

In one embodiment, which may be a transfemoral embodiment of the tissue cutting system, a flexible catheter is connected to the outer tubular member. In one embodiment the system also comprises a control device for controlling the resection device and/or other functions of the system. One example of a control device is shown in FIG. 12. The control device may be configured to control a number of functions e.g. the vacuum generator and/or application of the vacuum generator and/or application of fluid into the second fluid flow channel.

In order to improve the placement of the resection window, the inventor has also realized that in the narrow and challenging space where the cutting device operates it may be useful to be able to flex or bend the outer tubular member slightly to reach a part of tissue to be aspirated and cut. In one embodiment the tissue cutting system therefore further comprises a flex channel incorporated into the sidewall of the outer tubular member. A control device may be configured to control a flex wire in the flex channel for example such that when the wire is tightened it will cause a part of the outer tubular member to flex or bend slightly.

The at least one second fluid flow channel is/are suitable for regulating a pressure in the distal portion and/or assist the first fluid flow channel in transporting resected tissue. In a first aspect regulating a pressure in the distal portion may have the meaning that the pressure in the distal portion shall be maintained at substantially the same level as the pressure outside the device. This has the advantage that if the tool is used for surgery, for example resecting the hypertrophic septum of a heart, maintaining pressure inside the device substantially equal to the pressure outside prevents that material moves from the inside of the device out to the body and vice versa when the resection window is open. Therefore, in one embodiment of the present invention the at least one second fluid flow channel is suitable for regulating a pressure in the distal portion such that material does not flow between an outer area of the device and an inner area when the resection window is open.

Therefore, in one embodiment the device further comprises at least one pressure sensor. In a further embodiment, one sensor is located outside the device and one pressure sensor inside the device. The inside sensor may be located in the distal portion or the proximate portion of the outer tubular member, or in the distal end or proximal end of the inner tubular member, and the outside sensor may be located outside the outer tubular member. In one embodiment the pressure(s) is/are measured in real-time. Preferably the pressure in the distal portion is also regulated real-time by means of a pressure regulator connected to the second fluid flow channel. As stated above, the arterial pressure varies both within one cardiac cycle and over several cardiac cycles. As a consequence, the relative pressure between the distal portion or the proximate portion of the outer tubular member and an area outside the device, e.g. in the aorta or left ventricle, also varies. The presently disclosed tissue cutting device, having at least one pressure sensor, can be used in heart surgery without arresting the heart, in particular involving resection of a part of the hypertrophic septum. By compensating a difference in pressure between the outside and inside of the device based on data from the sensors, it can be prevented that liquid enters or leaves the device involuntarily and that resected tissue is released in the blood circulation. In one embodiment the outside pressure is calculated as an average pressure value over a cardiac cycle.

In one embodiment of the present invention, the at least one second fluid flow channel is configured to assist the first fluid flow channel in transporting resected tissue away from the resection element through the first fluid flow channel when the resection window is closed. This is achieved by increasing the pressure in the second fluid flow channel when the resection window is closed. The first fluid flow channel and the second fluid flow channel can then be seen as a closed system of channels. If the second fluid flow channels contains a liquid, such as water, or a saline solution, or a glucose solution, to regulate the pressure, the liquid will flow from the second fluid flow channel to the first fluid flow channel. In one embodiment the at least one second fluid flow channel is configured to flush resected tissue away from the distal portion through the first fluid flow channel, wherein the pressure regulator is configured to generate a flow of liquid through the at least one second fluid flow channel towards the distal portion, the flow of liquid continuing from the distal portion away from the distal portion through the first fluid flow channel.

The device may have more than one second fluid flow channel for several reasons. One reason may be that the pressure can be regulated more efficiently if there are several channels. For example, in a configuration where resected tissue is flushed away from an area adjacent to the resection element, the second fluid flow channel may be located such that liquid flows from several directions towards the resected tissue. Another reason for having more than one second fluid flow channel is to separate the pressure regulating function when the resection window is open and the flushing function when the resection window is closed. Therefore, in one embodiment a primary channel of the at least one second fluid flow channels is suitable for regulating a pressure in the distal portion, and a secondary channel of the at least one second fluid flow channels is configured to flush resected tissue away from the distal portion through the first fluid flow channel.

The tissue cutting device may further comprise one or more transmitter(s) and/or transducer(s) configured to indicate the location of the tissue cutting device. In one embodiment, the transmitter(s)/transducer(s) is/are ultrasonic transmitter(s)/transducer(s). The advantage of having transmitter(s)/transducer(s) on the device is that when the tool is used for surgery, for example resection of the hypertrophic septum of a heart, the tool is typically not directly visible to the surgeon. Since the positioning of the tool can be crucial, the transmitters constitute a means to track the location of the device in relation to the septal part of the heart. The transmitter(s) may be located anywhere on the device. In a preferred embodiment, the transmitter(s) is/are located at the closed distal end of the outer tubular member, either inside or outside the device.

Application

The tissue cutting device according to the presently disclosed invention is primarily a surgical instrument.

As stated, septal hypertrophy is the medical term used when the septum dividing the right and left ventricle of the heart is hypertrophic, i.e. thicker than normally. Surgical myectomi is done by routine open heart surgery, where the chest is opened by a median sternotomy, the patient is put on heart-lung machine and the heart is arrested. The tissue cutting device according to the present invention is suitable for use as a surgical instrument configured to resect tissue of a human and/or animal heart. More specifically, the device is suitable for resecting the hypertrophic septum of a heart. In principle the device could also be used to cut other tissue, either with the intention of removing tissue or for sampling purposes (biopsy).

When used as a device for resecting the hypertrophic septum of a heart, the device is typically inserted in the heart through the apex of a heart or inserted through the vasculature of the body, such as the femoral artery, ascending aorta or subclavian artery. Inserting the tissue cutting device for resection of the hypertrophic septum of a heart can be done as for any intra-arterial device and is known to those skilled in the art.

Method for Resecting Tissue

A further aspect of the presently disclosed invention relates to a method for resecting tissue using the tissue cutting system according to the present disclosure, comprising the steps of:
    positioning the resection window adjacent to tissue to cut;
    generating a vacuum pressure;
    connecting the vacuum pressure to the first fluid flow channel, thereby aspirating tissue through the resection window;
    measuring and analysing the pressure in the first fluid channel for a predefined period of time; and
    if the measured period remains below a predefined pressure threshold for longer than a predefine period of time, sliding the resection element thereby cutting tissue, otherwise disconnecting the vacuum pressure to the first fluid flow channel.

By using the at least one pressure sensor of the tissue cutting system it is possible to implement a method that is capable of cutting tissue while avoiding that substantially any blood is aspirated from the heart or blood circulation during the surgery. In the method, typically a vacuum generator is initially activated. In principle, the vacuum generator is preferably enabled throughout the process. Quick generation of vacuum is typically generated by building up an external vacuum and then connecting the generated vacuum to the first fluid flow channel. In a typical process the resection window is therefore placed adjacent to, preferably directly on, the tissue to be resected. At some point the generated vacuum is connected to the first fluid flow channel, which will cause the pressure to fall rapidly and aspirate tissue through the resection window. The pressure is measured continuously in the first fluid flow channel and possibly monitored or analyzed automatically. If the pressure remains at a low level, i.e. below a predefined threshold it corresponds to the tissue filling the whole resection window without any substantial leakage. If this is the case the resection element can be controlled (slid) to cut the tissue extending through the tissue resection window. If, on the other hand, the pressure does not go below the predefined threshold or returns to a higher level, it shows that there is a leakage and there is a risk that blood is aspirated. In this case the vacuum should be disconnected.

Furthermore a method for resecting tissue using the tissue cutting device as described, comprising the steps:
    opening the tissue resection window and during and after the opening regulating the pressure in the distal portion through the at least one second fluid flow channel such that the pressure is substantially equal to the pressure outside the tissue cutting device;
    activate a vacuum generator connected to the first fluid flow channel such that tissue located outside the cutting device is aspirated into the distal portion of the outer tubular member through the tissue resection window;
    closing the tissue resection window by sliding the inner tubular member in an axial direction lengthwise of the outer tubular member towards the closed distal end, the resection element thereby resecting tissue extending through the tissue resection window;
    increasing the pressure in the outer channel to generate a flow of liquid through the outer channel towards the distal portion, the flow of liquid continuing from the distal portion away from the distal portion through the first fluid flow channel.

FIGS. 4A-4B may serve as an illustration of the method. In FIG. 4A the resection window (202) is open. Hence, the first step, opening the tissue resection window, has already been done at this point. The step of regulating the pressure in the distal portion through the at least one second fluid flow channel such that the pressure is substantially equal to the pressure outside the tissue cutting device is not shown in FIG. 4A. In FIG. 4A, a vacuum generator connected to the first fluid flow channel has been activated to aspirate tissue (209) into the distal portion of the outer tubular member through the tissue resection window. It can be seen in FIG. 4A how tissue (209) extends through the resection window. An arrow indicates that the inner tubular member (203) is about to slide to the left in the drawing, thereby closing the tissue resection window and resecting tissue extending through the tissue resection window. At approximately the same time as the same time as the resection window closes, the pressure in the second fluid flow channel (206) is increased to generate a flow of liquid through the outer channel towards the distal portion, which is shown in FIG. 4B. FIG. 4B shows how a flow of liquid is generated from the second fluid flow channel (206) towards the distal portion and further on to the first fluid flow channel (205), thereby assisting in transporting the tissue (209) away from the distal portion through the first fluid flow channel (205).

The vacuum generator does not necessarily have to generate absolute vacuum. Vacuum in this sense does not mean absolute vacuum, but includes partial vacuum, i.e. any negative pressure between the original pressure and absolute vacuum. In a preferred embodiment the vacuum generator is configured to decrease the pressure in the inner tubular member rapidly.

Typical use involves repeating the steps of the method for resecting tissue. Therefore, a complete sequence of steps to resect and remove tissue typically includes the step of positioning the device such that the resection window is located adjacent to or in direct contact with the tissue to resect, executing the steps of the disclosed method for resecting tissue, resetting the pressure in the first and second fluid flow channels, re-positioning the device adjacent to a new piece of tissue to resects, and so forth until the desired amount of tissue has been removed.

Tissue Removal Device

Figure 9:
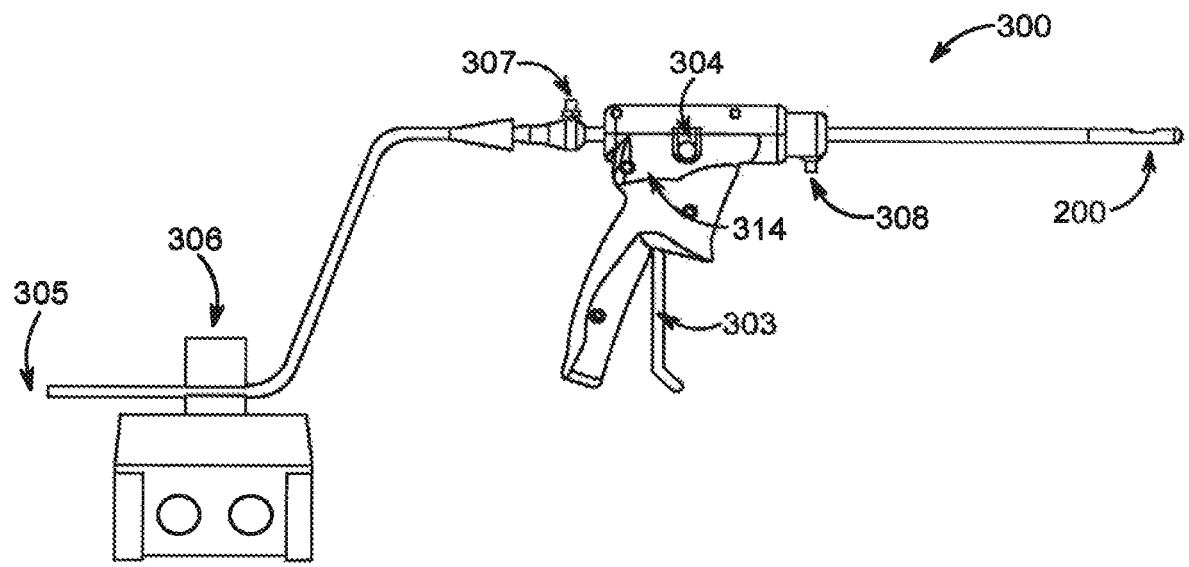
FIG. 9 shows another embodiment of a tissue cutting device according to the present invention.

The presently disclosed invention further relates to a tissue removal device comprising the tissue cutting device, the tissue removal device further comprising: a vacuum generator; a collector for collecting the resected tissue; an actuator for controlling a sliding movement of the inner tubular member along the outer tubular member; and a housing. FIG. 9 show an example of such a tissue removal device. The vacuum generator (305) is not shown explicitly but pointed; however its position in the system is indicated and its connection through a pipe to the first fluid channel of the tissue cutting device (200).

Figure 10:
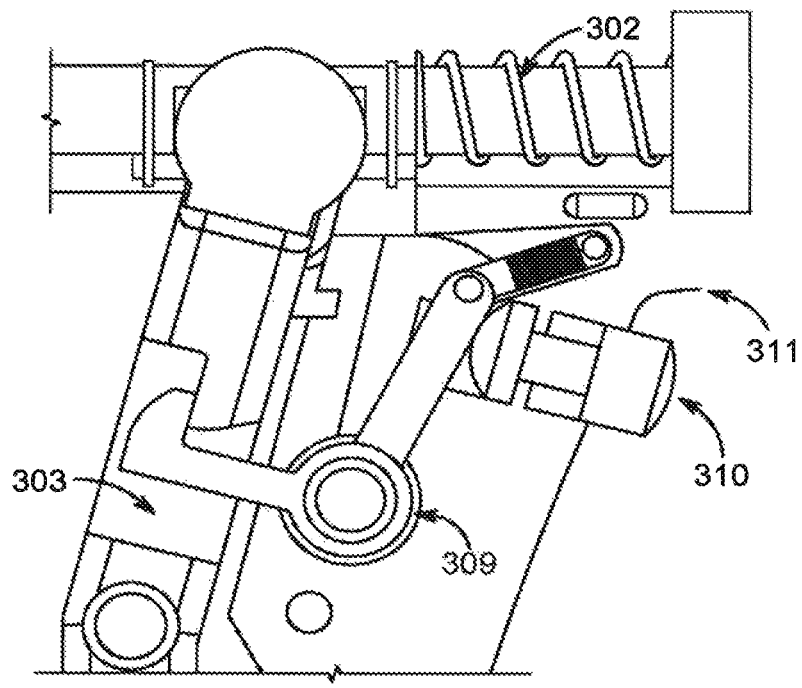
FIG. 10 shows a mechanical solution of the tissue cutting device, configured to control the inner tubular member.

The tissue removal device may include a lever mechanism configured for pushing the inner tubular member in an axial direction lengthwise of the outer tubular member towards the closed distal end, wherein the lever is connected to the actuator. FIG. 10 shows an example of such a lever mechanism.

In a preferred embodiment the tissue removal device further comprises a regulating system for regulating the pressure in the distal portion and regulating the secondary pressure in the first tubular member and distal portion controlled by the vacuum generator.

DETAILED DESCRIPTION OF THE DRAWINGS

Figure 1A:
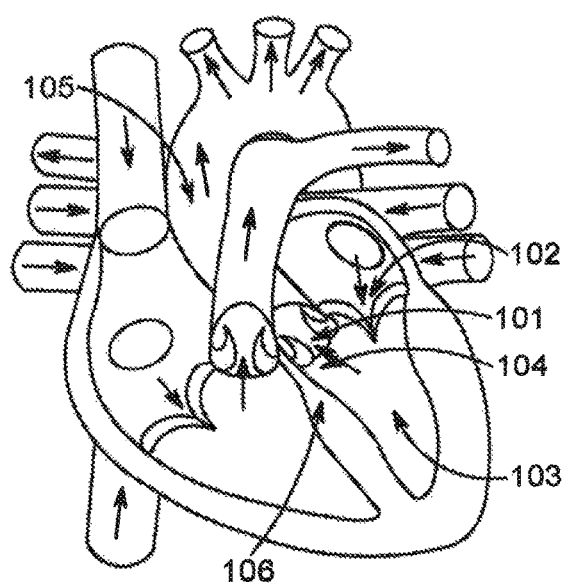
FIGS. 1A-1B show two versions of a transection of a heart.
Figure 1B:
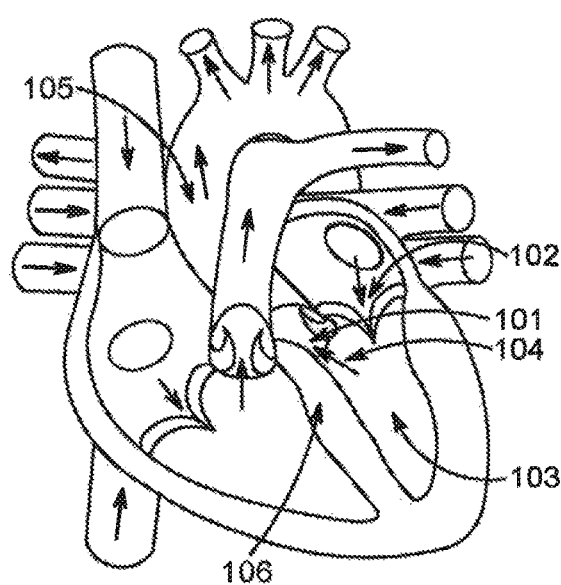

FIGS. 1A-1B show two versions of a transection of a heart. FIG. 1A shows a transection of a normal heart. FIG. 1B shows a transection of a heart having a hypertrophic septum. When the aortic valve (101) opens, blood goes from the left ventricle (103) into the aorta (105). The outflow tract (104) of the left ventricle is a portion through which blood passes in order to enter the aorta (105). The mitral valve (102) is a dual-flap valve between the left atrium and the left ventricle (103). The septum (106) between the left and right ventricle can be considered normal in FIG. 1A and enlarged in FIG. 1B, thereby protruding into the outflow tract (104) in the latter.

Figure 2A:
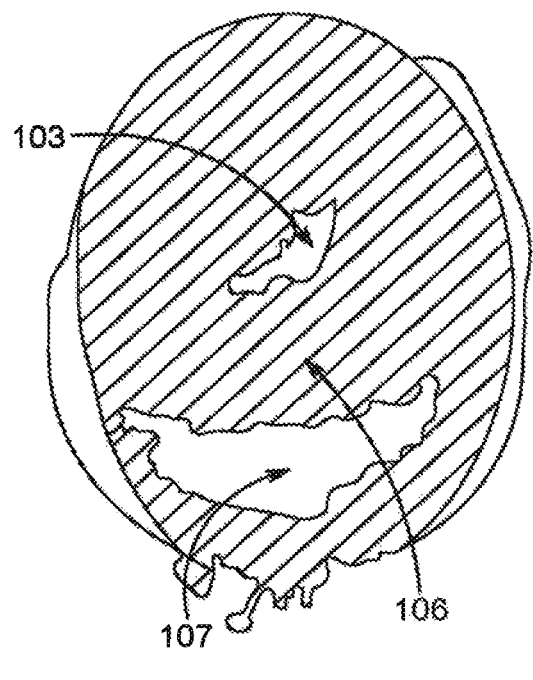
FIGS. 2A-2B show two versions of a transverse section of a porcine heart.
Figure 2B:
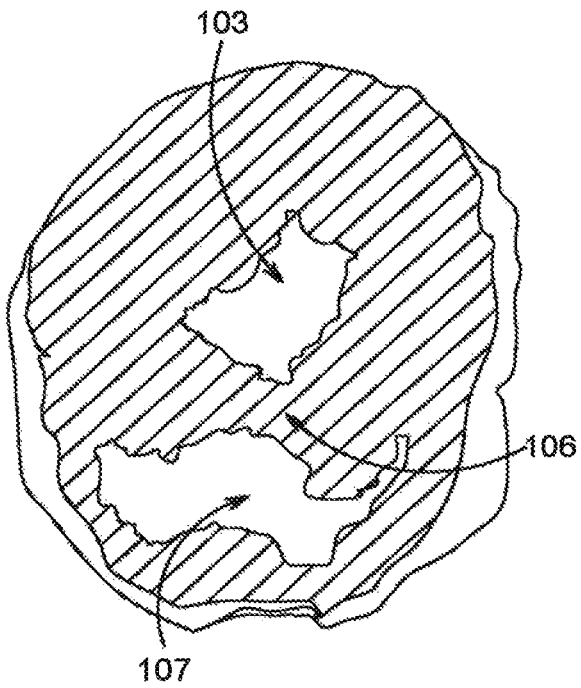

FIGS. 2A-2B show two versions of a transverse section of a porcine heart. FIG. 2A shows an untreated heart and FIG. 2B shows a heart where tissue has been removed from the septal part. The drawings show the shapes and positions of the left ventricle (103), the right ventricle (107), and the septum (106). In FIG. 2B tissue has been removed from the septum (106).

FIGS. 3A-3B show an embodiment of the tissue cutting device (200). In FIG. 3A the resection window (202) is closed and in FIG. 3B the resection window (202) is open. The device has an outer tubular member (201) (with a distal portion (210)), a distal end (207), an inner tubular member (203) and a resection element (204). The tubular members form a first fluid flow channel (205) and a second fluid flow channel (206). The resection window (202) has a sloping edge (208).

FIGS. 4A-4B show another embodiment of the tissue cutting device (200). The figures illustrate how tissue (209) is aspirated (FIG. 4A) into the distal portion of the device and transported away (FIG. 4B) from the resection element through the first fluid flow channel (205). The device has an outer tubular member (201) (with a distal portion (210)), an inner tubular member (203) and a resection element (204). The tubular members form a first fluid flow channel (205) and a second fluid flow channel (206). The resection window (202) has a sloping edge (208).

Figure 5:
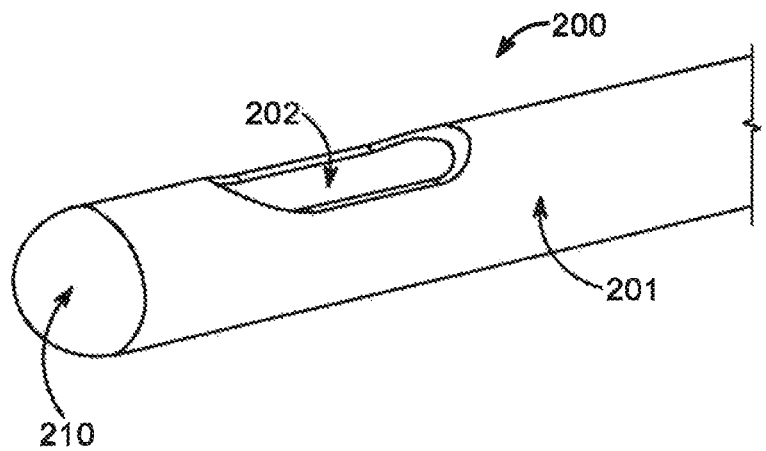
FIG. 5 shows an embodiment of the tissue cutting system, wherein the outer tubular member has a plug at the distal end.

FIG. 5 shows an embodiment of the tissue cutting device (202) having a resection window (202), wherein the outer tubular member (201) has a plug (210) at the distal end.

Figure 6:
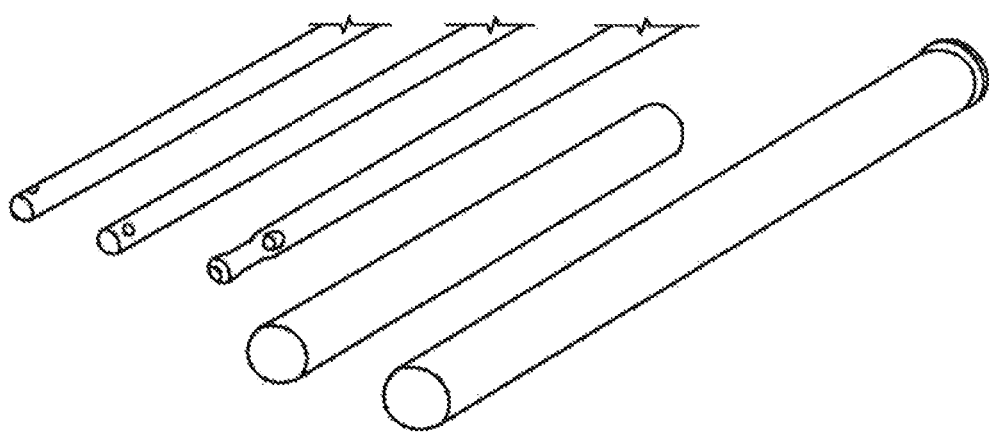
FIG. 6 shows a selection of outer tubular members made in one piece

FIG. 6 shows a selection of outer tubular members made in one piece.

FIGS. 7A-7C show three different resection elements. In these examples, the resection elements are integrated parts of the inner tubular member (203), having cutting surfaces (211) of different shapes, such as oval inside-oval outside (FIG. 7A), pointed inside-pointed outside (FIG. 7B) and oval inside-pointed outside (FIG. 7C).

Figure 8:
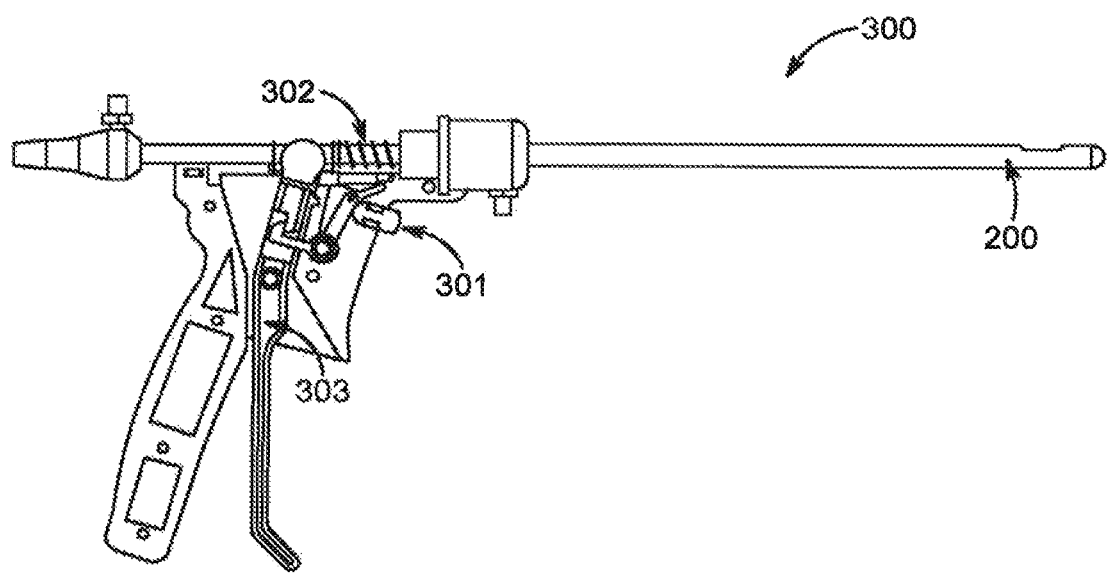
FIG. 8 shows an embodiment of a tissue cutting device according to the present invention.

FIG. 8 shows an embodiment of a tissue cutting system (300) according to the present invention, having a tissue cutting device (200), a trigger (301), a lever (303) and a spring (302) for pushing the resection element backwards to open the resection window.

FIG. 9 shows another embodiment of a tissue cutting system (300) according to the present invention, having a tissue cutting device (200), a lever (303), a vacuum activator (304), a liquid inlet (308), a housing (314), a manometer connection (307), a pinch valve (306). There is no vacuum source shown in the system; however 305 is an indication of where a vacuum source would be connected.

FIG. 10 shows a mechanical solution of the tissue cutting system, configured to control the inner tubular member, including a lever (303), a spring (302), a trigger pivot (309), a trigger button (310) and a trigger release spring (311).

Figure 11:
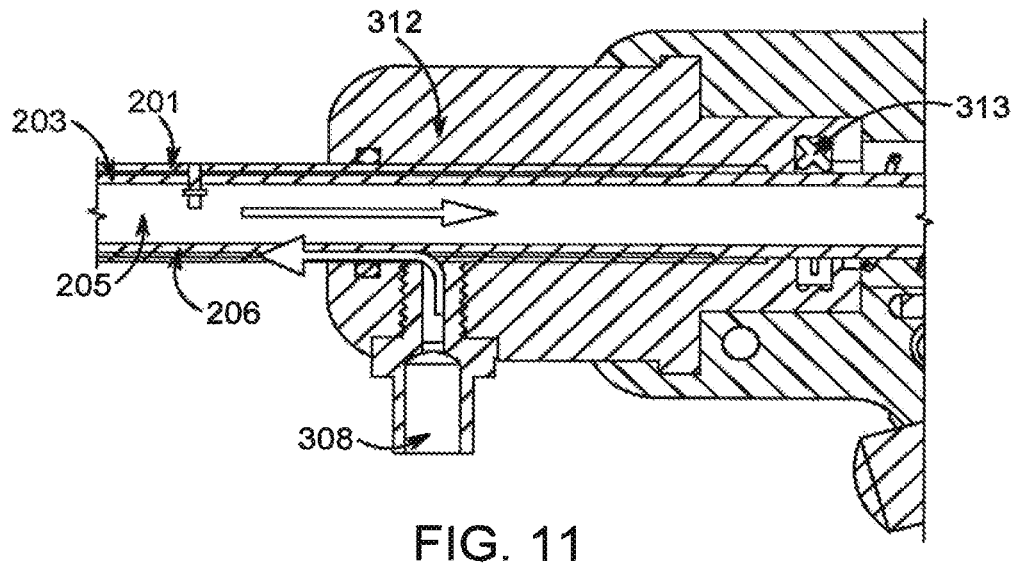
FIG. 11 shows a part of one embodiment of the tissue cutting device, comprising a collet to stabilize the movement of the inner tubular member and to seal the flow of liquid within the intended premises.

FIG. 11 shows a part of one embodiment of the tissue cutting system, comprising a collet (312) to stabilize the movement of the inner tubular member (203) and to seal the flow of liquid within the intended premises. The tissue removal device has a luer connector liquid flow (308) and a quad-ring (313).

FIG. 12 shows one embodiment of the tissue cutting system having a catheter (318) connected between a tissue cutting device (200) and a control device (314). A guidewire (316) (having a guidewire tip 316) extends through the tissue cutting device (200) and the catheter (318). The length of the catheter may be adapted to e.g. transfemoral use of the system for cutting tissue of a heart. The control device (314) comprises flex control (319) for flexing of cutting device (200), a cutting control handle (304), a flush fluid port (324), pressure control port (325) for controlling the resection element, a vacuum port (320), and a release button (322) for applying a generated vacuum to the first fluid flow channel.

Figure 13:
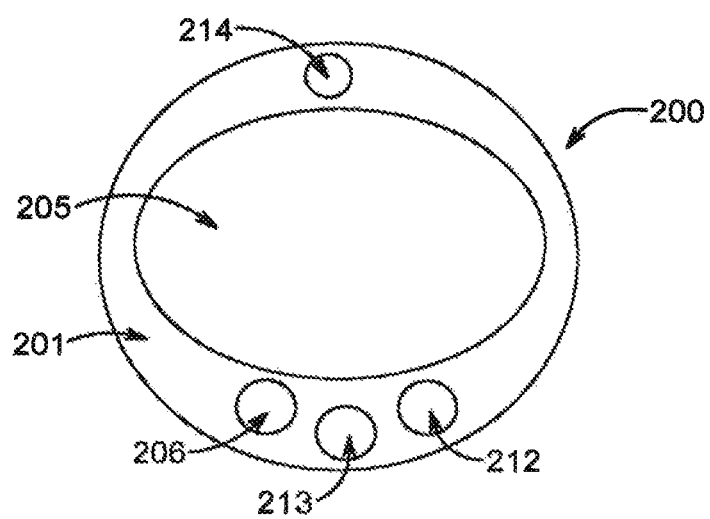
FIG. 13 shows a cross-section of one embodiment of the tissue cutting system having first and second fluid flow channels, further comprising a third resection element control channel, a fourth guidewire channel and a fifth flex channel.

FIG. 13 shows a cross-section of one embodiment of the tissue cutting system (200) having first (205) and second (206) fluid flow channels, further comprising a third resection element control channel (212), a fourth guidewire channel (213) and a fifth flex channel (214).

FIG. 14 shows a further embodiment of the tissue cutting system (200) having a backwardly cutting resection element (204). A plunger (216) and the outer tubular member (201) define a chamber (215) which can be used to push or retract the plunger (216) by regulating the pressure inside the chamber through the resection element control channel (212). The outer tubular member (201) also form a first fluid flow channel (205) configured to transport tissue away from a region adjacent to the resection window (202). In the example the second fluid flow channel (206) is incorporated in the sidewall of the outer tubular member.

Figure 15A:
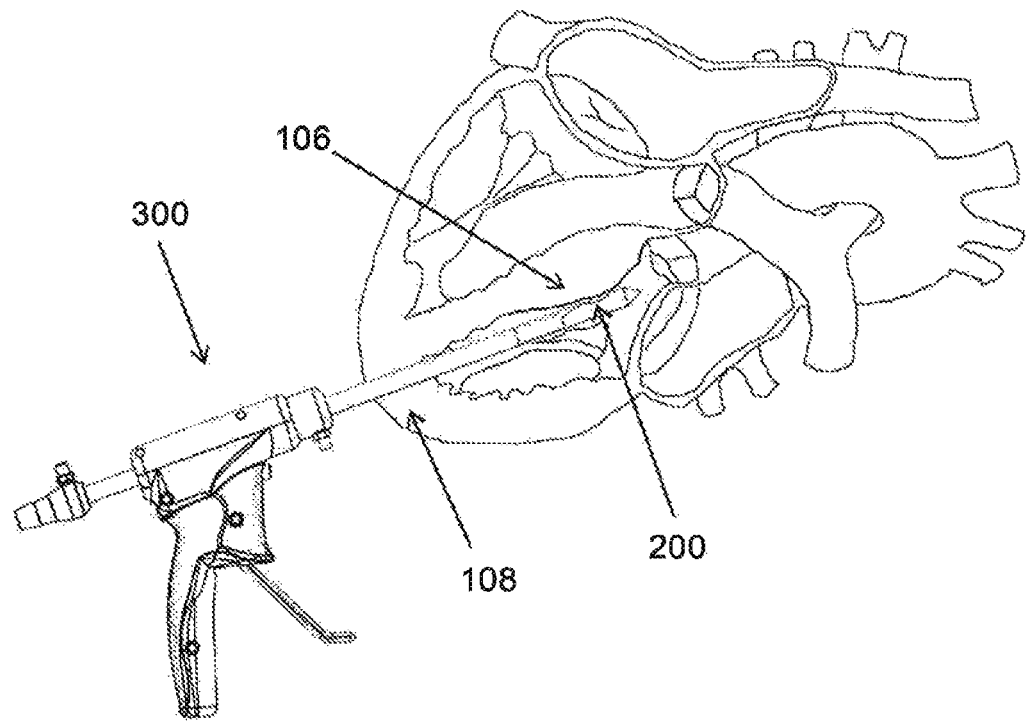
FIGS. 15A-15B-b show examples of usage of the tissue cutting system.
Figure 15B:
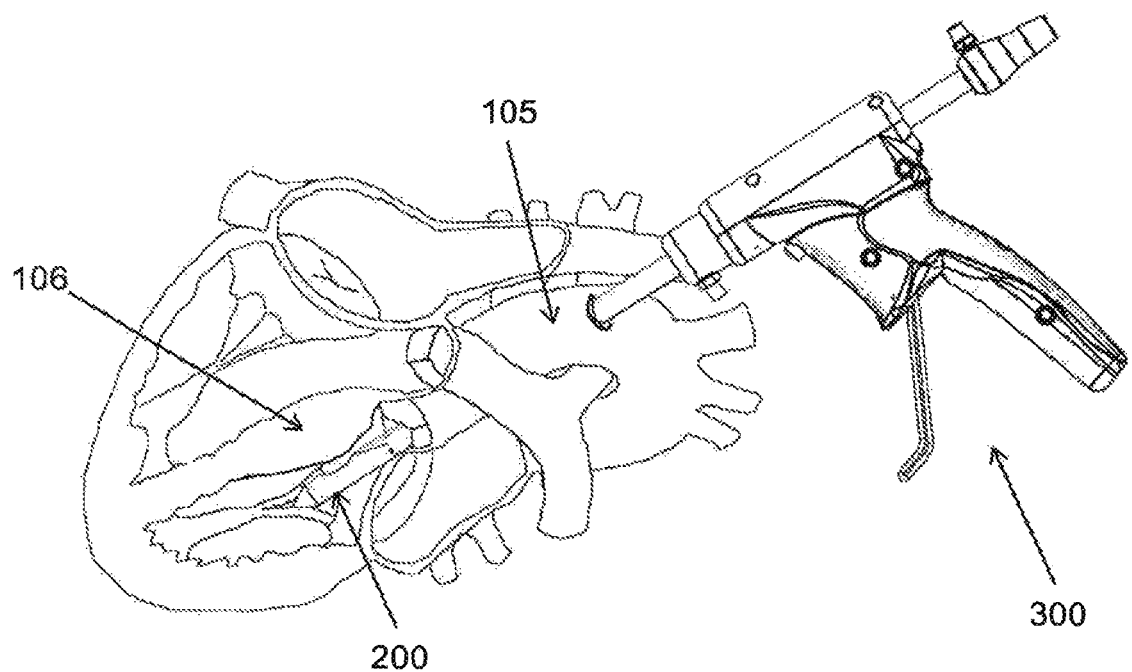

FIGS. 15A-15B show examples of usage of the tissue cutting system (300). In FIG. 15A the device is inserted through the apex (108) and in FIG. 15B the device is inserted through the aorta (105).

Figure 16:
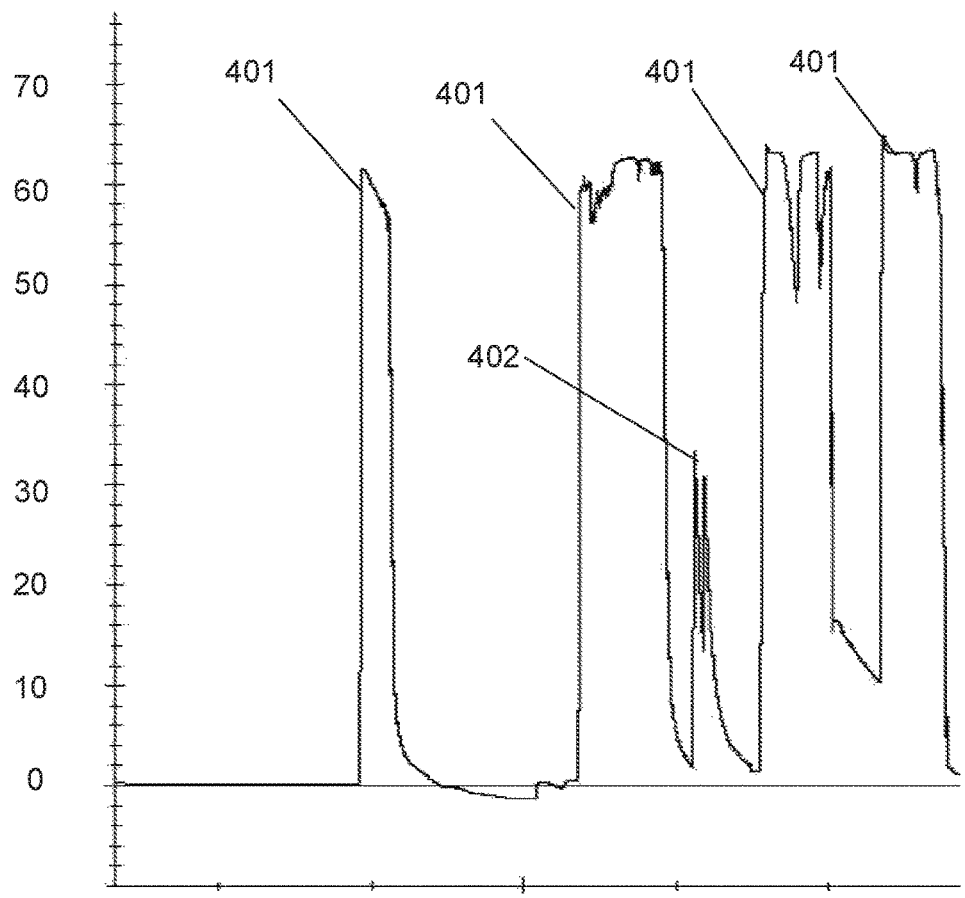
FIG. 16 shows a pressure diagram for an operating scenario of the tissue cutting system.

FIG. 16 shows a pressure diagram for an operating scenario of the tissue cutting system. It can be noted that the pressure, shown as a function of time, is inverted, which means that a higher value corresponds to a lower pressure. The displayed scenario involves five attempts to apply a generated vacuum to a region adjacent to the resection window of the instrument. Four of the attempts to aspirate tissue without leakage are successful (401), which corresponds to that the pressure drops quickly when the vacuum is applied and stays low for a predefined amount of time until tissue is cut and the resection window is closed again. Peak 402 corresponds to an attempt wherein there is leakage or the resection window does not attach to the tissue to be resected when vacuum is applied. In this case the pressure drops quickly but does not remain on a low level. In this case the attempt is preferably interrupted and the resection window closed in order not to aspirate blood from the heart.

Figure 17:
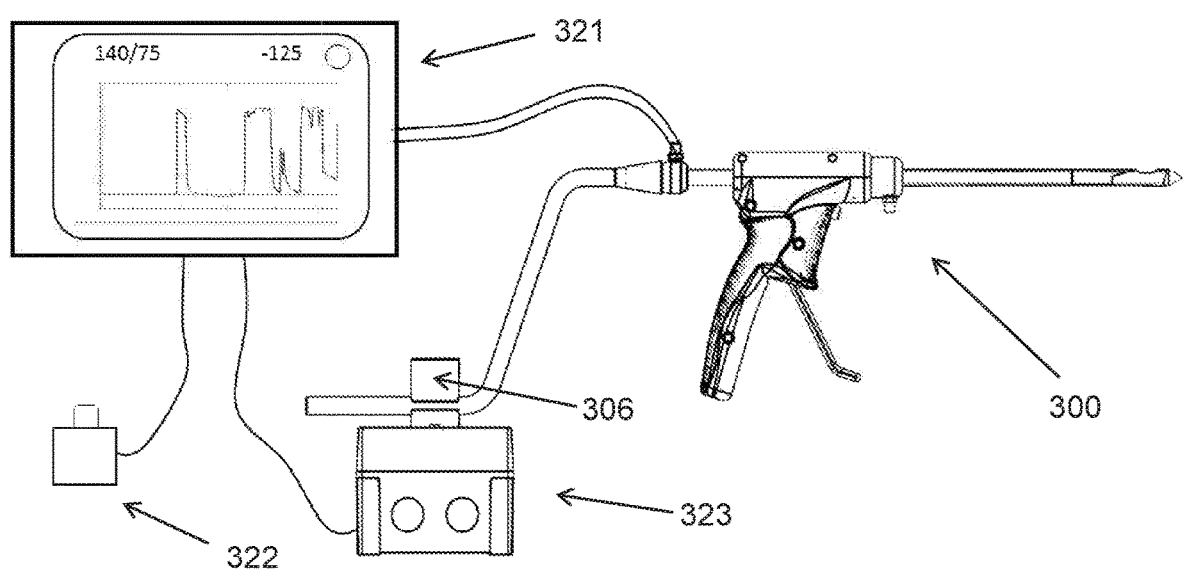
FIG. 17 shows a system for controlling and monitoring the operation of the tissue cutting system.

When the vacuum pressure is connected, e.g. by opening a valve, it will quickly be realized whether the resection window is filled with tissue without leakage FIG. 17 shows a system for controlling and monitoring the operation of the tissue cutting system (300). The pressure is measured and connected to monitoring means (321). Based on the measured pressure, the system can then, manually or automatically, control a vacuum generator (323) and a valve (306).

Further Details of the Invention

1. A tissue cutting device comprising:
    an outer tubular member having a proximal portion and a distal portion, said distal portion comprising a tissue resection window;
    an inner tubular member axially slidably arranged inside the outer tubular member; and
    a resection element configured to resect tissue extending through the tissue resection window,
    wherein the inner and outer tubular member are arranged to establish:
    a first fluid flow channel suitable for transporting resected tissue away from an area adjacent to the resection element;
    at least one second fluid flow channel suitable for regulating a pressure in the distal portion and/or configured to assist the first fluid flow channel in transporting resected tissue.

2. The tissue cutting device according to any of the preceding items, further comprising a pressure sensor.

3. The tissue cutting device according to any of the preceding items, further comprising an actuator for controlling a sliding movement of the resection element along the outer tubular member to resect tissue extending through the resection window.

4. The tissue cutting device according to any of the preceding items, wherein the at least one pressure sensor is in connection with the first fluid flow channel.

5. The tissue cutting device according to any of the preceding items, wherein the at least one pressure sensor is configured to measure a pressure inside the outer tubular member in a region adjacent to the tissue resection window.

6. The tissue cutting device according to any of the preceding items, further comprising a vacuum generator in connection with the first fluid flow channel.

7. The tissue cutting device according to any of the preceding items, further comprising processing means configured to determine whether the measured pressure is below a predetermined pressure threshold.

8. The tissue cutting device according to item 7, wherein the processing means is configured to determine whether the tissue to be resected fills the resection window when vacuum is applied in the first fluid flow channel based on the measured pressure.

9. The tissue cutting device according to any of items 7-8, wherein the processing means is configured to determine whether the measured pressure is below a predetermined pressure threshold for longer than a predefine period of time when vacuum is applied in the first fluid flow channel based on the measured pressure.

10. The tissue cutting device according to any of the preceding items, further comprising an inner tubular member.

11. The tissue cutting device according to item 10, wherein the inner tubular member is axially slidably arranged inside the outer tubular.

12. The tissue cutting device according to any of the preceding items, wherein the resection element is configured to cut tissue backwards towards a direction from the distal portion towards the proximal portion.

13. The tissue cutting device according to any of the preceding items, wherein the resection element is located distally to the resection window when the resection window is open.

14. The tissue cutting device according to any of the preceding items, further comprising a plunger sealingly engaged inside the outer tubular member.

15. The tissue cutting device according to item 14, wherein the plunger is an integral part of the resection element.

16. The tissue cutting device according to any of items 14-15, further comprising a resection element control channel incorporated into the sidewall of the outer tubular member, wherein the resection element control channel is fluid connection with a closed chamber defined by the outer tubular member and the plunger.

17. The tissue cutting device according to item 16, wherein the system is configured to control a fluid in the closed chamber such that when a chamber pressure in the chamber is increased a backwards movement of the resection element is produced and when the chamber pressure is decreased a forwards movement of the resection element is produced.

18. The tissue cutting device according to any of the preceding items, further comprising a guidewire channel incorporated into the sidewall of the outer tubular member.

19. The tissue cutting device according to according to item 18, further comprising a guidewire arranged inside the guidewire channel extending from a proximal end of the outer tubal member to a distal end of the outer tubular member.

20. The tissue cutting device according to any of the preceding items, further comprising a flexible catheter connected to the outer tubular member and a control device.

21. The tissue cutting device according to item 20, wherein the control device is configured to control the resection element and/or the vacuum generator and/or application of the vacuum generator and/or application of fluid into the second fluid flow channel.

22. The tissue cutting device according to any of the preceding items, further comprising a flex channel incorporated into the sidewall of the outer tubular member.

23. The tissue cutting device according to any of the preceding items, wherein the control device is configured to control a flex wire in the flex channel.

24. The tissue cutting device according to any of the preceding items, wherein resected tissue is aspirated from the area adjacent to the resection element through the first fluid flow channel.

25. The tissue cutting device according to any of the preceding claims, wherein the resection window is located proximate to a closed distal end of the outer tubular member, such as less than 0.1 mm, or less than 0.2 mm, or less than 0.3 mm, or less than 0.4 mm, or less than 0.5 mm, or less than 1.0 mm, or less than 2.0 mm, or less than 3.0 mm, or less than 4.0 mm, or less than 5.0 mm, or less than 10 mm, or less than 15 mm, or less than 20 mm, or less than 25 mm, or less than 30 mm.

26. The tissue cutting device according to any of the preceding items, wherein the resection window has a length of less than 3 mm, or less than 4 mm, or less than 5 mm, or less than 6 mm, or less than 7 mm, or less than 8 mm, or less than 9 mm, or less than 10 mm, or less than 15 mm, or less than 20 mm, or less than 25 mm, or less than 30 mm, or less than 50 mm.

27. The tissue cutting device according to any of the preceding items, wherein the resection window extends over a portion of a circumference of the outer tubular member, such as less than 5% of the circumference, or less than 6% of the circumference, or less than 7% of the circumference, or less than 8% of the circumference, or less than 9% of the circumference, or less than 10% of the circumference, or less than 15% of the circumference, or less than 20% of the circumference, or less than 30% of the circumference, or less than 40% of the circumference, or less than 50% of the circumference, or less than 60% of the circumference.

28. The tissue cutting device according to any of the preceding items, said resection window having an edge sloping downwards towards the center of the resection window.

29. The tissue cutting device according to any of the preceding items, wherein the resection element is an integrated part of the inner tubular member.

30. The tissue cutting device according to any of the preceding items, the inner tubular member having a hollow interior defining the first fluid flow channel extending from an open proximal end of the inner tubular member to an open distal end of the inner tubular member, said open distal end comprising a cutting surface defining an acute angle to the longitudinal axis of the inner tubular member, forming a substantially oval edge of the inner tubular member.

31. The tissue cutting device according to any of the preceding items, wherein the inner tubular member is a tissue penetrating cannula, wherein the open distal end is sharp.

32. The tissue cutting device according to item 31, wherein the acute angle is between 1° and 30°.

33. The tissue cutting device according to any of items 31-32, wherein the cannula is a lancet cannula having a sharpened front.

34. The tissue cutting device according to any of the preceding items, wherein an upper side of the resection element is configured to slide smoothly along the inside of the outer tubular member, thereby cutting tissue extending through the tissue resection window.

35. The tissue cutting device according to any of the preceding items, wherein the open distal end comprises a scalpel or razor blade.

36. The tissue cutting device according to any of the preceding items, wherein the inner tubular member, including the resection element, is made of one piece.

37. The tissue cutting device according to any of the preceding items, wherein the at least one second fluid flow channel is a space between the outer tubular member and the inner tubular member.

38. The tissue cutting device according to any of the preceding items, the at least one second fluid flow channel having the shape of an annular tube.

39. The tissue cutting device according to any of the preceding items, wherein the at least one second fluid flow channel is located in the opposite side of a cross-section of the outer tubular member in relation to the resection window.

40. The tissue cutting device according to any of the preceding items, wherein the at least one second fluid flow channel is incorporated into the sidewall of the outer tubular member.

41. The tissue cutting device according to any of the preceding items, the cutting device having one or more additional fluid flow channels.

42. The tissue cutting device according to any of the preceding items, the cutting device having a device outer diameter between 2 mm and 20 mm, or between 2 mm and 15 mm, or between 2 mm and 10 mm, or between 5 mm and 10 mm, or between 5 mm and 15 mm, such as 2 mm, or 3 mm, or 4 mm, or 5 mm, or 6 mm, or 7 mm, or 8 mm, or 9 mm, or 10 mm, or 11 mm, or 12 mm, or 13 mm, or 14 mm, or 15 mm, or 16 mm, or 17 mm, or 18 mm, or 19 mm, or 20 mm.

43. The tissue cutting device according to any of the preceding items, the inner tubular member having an inner tubular inner diameter between 1 mm and 10 mm, or between 1 mm and 7 mm, or between 1 mm and 5 mm, or between 1 mm and 3 mm, such as 1 mm, or 2 mm, or 3 mm, or 4 mm, or 5 mm, or 6 mm, or 7 mm, or 8 mm, or 9 mm, or 10 mm, or 12 mm, or 14 mm, or 16 mm, or 18 mm, or 19 mm.

44. The tissue cutting device according to any of the preceding items, wherein the difference between an inner tubular outer diameter of the inner tubular member and an outer tubular inner diameter is less than 5 mm, or less than 4 mm, or less than 3 mm, or less than 2 mm, or less than 1 mm, or less than 0.5 mm, or less than 0.4 mm, or less than 0.3 mm, or less than 0.2 mm, or less than 0.1 mm.

45. The tissue cutting device according to any of the preceding items, the device having a length of between 50 mm and 500 mm, or between 50 mm and 400 mm, or between 100 mm and 300 mm, or between 50 mm and 200 mm, or between 100 mm and 200 mm, or greater than 200 mm.

46. The tissue cutting device according to any of the preceding items, further comprising at least one additional tubular member inside the inner tubular member or outside the outer tubular member.

47. The tissue cutting device according to any of the preceding items, wherein the tissue cutting device is made of a rigid material, selected from the group of ceramics, ceramic composites, metal, such as aluminium or steel, or plastics, such as polycarbonate (PC) or polymethylmethacrylate (PMMA).

48. The tissue cutting device according to any of the preceding items, wherein the closed distal end is rounded or substantially pointed.

49. The tissue cutting device according to any of the preceding items, wherein the first fluid flow channel is configured to be connected to a vacuum source configured to establish a fluid flow to aspirate resected tissue away from an area adjacent to the resection element through the channel.

50. The tissue cutting device according to any of the preceding items, wherein the first fluid flow channel is suitable for transporting resected tissue away from the resection element.

51. The tissue cutting device according to any of the preceding items, further comprising at least one pressure sensor.

52. The tissue cutting device according to item 51, wherein the at least one pressure sensor is located in the distal portion or the proximate portion of the outer tubular member, or in the distal end or proximal end of the inner tubular member.

53. The tissue cutting device according to any of items 51-52, wherein the at least one pressure sensor is located outside the outer tubular member.

54. The tissue cutting device according to any of the preceding items, wherein the at least one second fluid flow channel is configured to uphold a pressure in the distal portion such that the pressure is substantially equal to the pressure outside the tissue cutting device when the resection window is open.

55. The tissue cutting device according to item 54, wherein the pressure outside the tissue cutting device a measured in real-time.

56. The tissue cutting device according to any of the preceding items, wherein the at least one second fluid flow channel is suitable for regulating a pressure in the distal portion such that material does not flow between an outer area of the device and an inner area when the resection window is open.

57. The tissue cutting device according to any of the preceding items, wherein the at least one second fluid flow channel contains a liquid, such as water, or a saline solution, or a glucose solution, to regulate the pressure.

58. The tissue cutting device according to any of the preceding items, wherein the at least one second fluid flow channel is configured to be connected to a pressure regulator.

59. The tissue cutting device according to any of the preceding items, wherein the at least one second fluid flow channel is configured to assist the first fluid flow channel in transporting resected tissue away from the resection element through the first fluid flow channel when the resection window is closed.

60. The tissue cutting device according to any of the preceding items, wherein the at least one second fluid flow channel is configured to flush resected tissue away from the distal portion through the first fluid flow channel, wherein the pressure regulator is configured to generate a flow of liquid through the at least one second fluid flow channel towards the distal portion, the flow of liquid continuing from the distal portion away from the distal portion through the first fluid flow channel.

61. The tissue cutting device according to any of the preceding items, wherein a primary channel of the at least one second fluid flow channels is suitable for regulating a pressure in the distal portion, and a secondary channel of the at least one second fluid flow channels is configured to flush resected tissue away from the distal portion through the first fluid flow channel.

62. The tissue cutting device according to any of the preceding items, wherein the cutting device is surgical instrument configured to resect tissue of a heart.

63. The tissue cutting device according to any of the preceding items, wherein the cutting device is surgical instrument configured to resect tissue of a human and/or animal tissue.

64. The tissue cutting device according to any of the preceding items, wherein the cutting device is configured to resect the hypertrophic septum of a heart.

65. The tissue cutting device according to any of the preceding items, wherein the cutting device is configured to be inserted through the apex of a heart.

66. The tissue cutting device according to any of the preceding items, wherein the cutting device is configured to be inserted through the vasculature of the body, such as the femoral artery, ascending aorta, subclavian artery or any other great vessel of the body.

67. The tissue cutting device according to any of the preceding items, further comprising a flexible section attached to the device, said flexible section configured to pass through any great vessel of the body.

68. The tissue cutting device according to any of the preceding items, further comprising a guidewire configured to guide the tissue cutting device to a position inside the body.

69. The tissue cutting device according to any of the preceding items, further comprising an introducer configured to introduce the tissue cutting device into any part or organ of the body, such as the heart.

70. The tissue cutting device according to any of the preceding items, further comprising one or more transmitter(s) and/or transducer(s) configured to indicate the location of the tissue cutting device.

71. The tissue cutting device according to item 70, wherein the transmitter(s)/transducer(s) is/are ultrasonic transmitter(s)/transducer(s).

72. The tissue cutting device according to any of items 70-71, wherein the transmitter(s)/transducer(s) is/are located at the closed distal end of the outer tubular member.

73. A method for resecting tissue using the tissue cutting device according to any of items 1-65, comprising the steps:
opening the tissue resection window and during and after the opening regulating the pressure in the distal portion through the at least one second fluid flow channel such that the pressure is substantially equal to the pressure outside the tissue cutting device;
activate a vacuum generator connected to the first fluid flow channel such that tissue located outside the cutting device is aspirated into the distal portion of the outer tubular member through the tissue resection window;
closing the tissue resection window by sliding the inner tubular member in an axial direction lengthwise of the outer tubular member towards the closed distal end, the resection element thereby resecting tissue extending through the tissue resection window;
increasing the pressure in the outer channel to generate a flow of liquid through the outer channel towards the distal portion, the flow of liquid continuing from the distal portion away from the distal portion through the first fluid flow channel.

74. The method according to item 73, wherein the liquid is water, or a saline solution, or a glucose solution.

75. The method according to any of items 73-74, wherein the vacuum generator is configured to generate a secondary (negative) pressure or partial or complete vacuum in the inner tubular member and distal portion, without delay, and wherein the secondary pressure is decreased rapidly.

76. The method according to any of items 73-75, wherein the steps of the method are repeated to resect several pieces of tissue.

77. The method according to any of items 73-76, wherein the tissue cutting device is assisted by transoesophageal or transthoracic echocardiography of the heart and/or fluoroscopy.

78. A method for resecting the hypertrophic septum of a heart according to the method of items 73-77.

79. A tissue removal device comprising the tissue cutting device according to any of items 1-65, the tissue removal device further comprising:
a vacuum generator;
a collector for collecting the resected tissue;
an actuator for controlling a sliding movement of the inner tubular member along the outer tubular member;
a housing.

80. The tissue removal device according to item 79, further comprising a regulating system for regulating the pressure in the distal portion and regulating the secondary pressure in the first tubular member and distal portion controlled by the vacuum generator.

81. The tissue removal device according to any of items 79-80, further comprising a lever mechanism configured for pushing the inner tubular member in an axial direction lengthwise of the outer tubular member towards the closed distal end, wherein the lever is connected to the actuator.

The invention claimed is:

1. A method for resecting tissue, comprising the steps of:
providing a tissue cutting system comprising:
an outer tubular member having a proximal portion and a distal portion, said distal portion comprising a tissue resection window;
a resection element axially slidably arranged inside the outer tubular member configured to resect tissue extending through the tissue resection window,
wherein the outer tubular member and resection element are arranged to establish:
a first fluid flow channel suitable for transporting resected tissue away from an area adjacent to the resection element;
at least one second fluid flow channel configured to assist the first fluid flow channel in transporting resected tissue,
positioning the resection window adjacent to tissue to cut;
generating a vacuum pressure;
connecting the vacuum pressure to the first fluid flow channel, thereby aspirating tissue through the resection window;
measuring and analysing the pressure in the first fluid channel for a predefined period of time; and
if the measured pressure remains below a predefined pressure threshold for longer than a predefined period of time, sliding the resection element, thereby cutting tissue, otherwise disconnecting the vacuum pressure to the first fluid flow channel.

2. The method for resecting tissue according to claim 1, wherein a pressure sensor provides the measured pressure in the first fluid flow channel.

3. The method for resecting tissue according to claim 1, further comprising a step of displaying the measured pressure as a function of time on a display.

4. The method for resecting tissue according to claim 1, further comprising a step of indicating to a user whether the measured pressure remains below a predefined pressure threshold for longer than a predefined period of time.

5. A method for securing a surgical tool having a tubular member, or a catheter, to tissue, the method comprising the steps of:
providing a surgical tool having a tubular member, or a catheter;
positioning an opening of the tubular member or catheter adjacent to the tissue;
generating a vacuum pressure;
connecting the vacuum pressure to the tubular member or catheter;
measuring and analysing the pressure in the tubular member or catheter for a predefined period of time; and
if the measured pressure remains below a predefined pressure threshold for longer than a predefined period of time, maintaining the vacuum in the tubular member or catheter to secure the surgical tool or catheter, otherwise disconnecting the vacuum pressure to the first fluid flow channel.

6. The method according to claim 5, further comprising a step of displaying the measured pressure as a function of time on a display.

7. The method according to claim 5, further comprising a step of indicating to a user whether the surgical tool or catheter has been secured to the tissue.

8. A system for securing a surgical tool having a tubular member, or a catheter, to tissue, the system comprising:
a surgical tool having a tubular member, or a catheter, the surgical tool or catheter comprising an opening;
a control device configured to assist a user in positioning the opening adjacent to the tissue;
at least one pressure sensor in connection with the tubular member or catheter;
a vacuum generator connected to the tubular member or catheter;
a processor configured to:
measure and analyze the pressure in the tubular member or catheter for a predefined period of time; and if the measured pressure remains below a predefined pressure threshold for longer than a predefined period of time, maintain the vacuum in the tubular member or catheter to secure the surgical tool or catheter, otherwise disconnect the vacuum pressure to the first fluid flow channel.

9. The system according to claim 8, wherein the processor is triggered to perform the steps of measuring and analyzing the pressure, and maintaining or disconnecting the vacuum pressure upon the opening being positioned adjacent to the tissue and vacuum being generated by the vacuum generator.

10. The system according to claim 8, further comprising a display for displaying the measured pressure as a function of time.

\* \* \* \* \*